United States Patent
Young-Dixon et al.

(10) Patent No.: US 11,413,461 B2
(45) Date of Patent: Aug. 16, 2022

(54) INDEPENDENT CONTROL OF ELECTRICAL STIMULATION AMPLITUDE FOR ELECTRODES FOR DELIVERY OF ELECTRICAL STIMULATION THERAPY

(71) Applicant: Medtronic, Inc., Minneapolis, MN (US)

(72) Inventors: Brendan J. Young-Dixon, St. Paul, MN (US); Alicia Weller Thompson, Coon Rapids, MN (US); Cheryl Peskar, Woodbury, MN (US); Lance Beall, Andover, MN (US); Susan Heilman Kilbane, Deephaven, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 183 days.

(21) Appl. No.: 16/694,549

(22) Filed: Nov. 25, 2019

(65) Prior Publication Data

US 2021/0154480 A1    May 27, 2021

(51) Int. Cl.
    *A61N 1/36*    (2006.01)
    *A61N 1/02*    (2006.01)
    *A61N 1/05*    (2006.01)

(52) U.S. Cl.
    CPC ......... *A61N 1/36157* (2013.01); *A61N 1/025* (2013.01); *A61N 1/0531* (2013.01); *A61N 1/36192* (2013.01)

(58) Field of Classification Search
    CPC .. A61N 1/36157; A61N 1/025; A61N 1/0531; A61N 1/36192; A61N 1/36185
    See application file for complete search history.

(56) References Cited

U.S. PATENT DOCUMENTS

| | | |
|---|---|---|
| 4,592,359 A | 6/1986 | Galbraith |
| 4,931,795 A | 6/1990 | Gord |
| 5,190,035 A | 3/1993 | Salo et al. |
| 5,241,472 A | 8/1993 | Gur et al. |
| 5,501,703 A | 3/1996 | Holsheimer et al. |
| 5,713,922 A | 2/1998 | King |

(Continued)

FOREIGN PATENT DOCUMENTS

| | | |
|---|---|---|
| EP | 2039391 A1 | 3/2009 |
| WO | 0154579 A1 | 8/2001 |

(Continued)

OTHER PUBLICATIONS

Bian et al., "Double electrodes simultaneous stimulation and implantation technique in deep brain stimulation," Chin J. Traumatol, vol. 8, Issue 4, pp. 253-256 8. (English translation of abstract only).

(Continued)

*Primary Examiner* — Paula J Stice
(74) *Attorney, Agent, or Firm* — Shumaker & Sieffert, P.A.

(57) ABSTRACT

Techniques are described, for medical devices that deliver electrical stimulation using current or voltage regulators having an adjustable master amplitude. One example method includes receiving, via a programmer for an electrical stimulator, user input indicating a desired electrical current amplitude, and selecting a first fraction adjustment or a second fraction adjustment, as a target adjustment for achieving the desired electrical current amplitude.

23 Claims, 10 Drawing Sheets

(56) References Cited

U.S. PATENT DOCUMENTS

| | | |
|---|---|---|
| 5,776,172 A | 7/1998 | Schulman et al. |
| 5,800,465 A | 9/1998 | Thompson et al. |
| 5,895,416 A | 4/1999 | Barreras, Sr. et al. |
| 5,916,238 A | 6/1999 | Hauser et al. |
| 5,954,758 A | 9/1999 | Peckham et al. |
| 6,341,234 B1 | 2/2002 | Thong et al. |
| 6,393,325 B1 | 5/2002 | Mann et al. |
| 6,421,564 B1 | 7/2002 | Yerich et al. |
| 6,505,078 B1 | 1/2003 | King et al. |
| 6,516,227 B1 | 2/2003 | Meadows et al. |
| 6,587,724 B2 | 7/2003 | Mann |
| 6,609,032 B1 | 8/2003 | Woods et al. |
| 6,625,482 B1 | 9/2003 | Panescu et al. |
| 6,799,070 B2 | 9/2004 | Wolfe et al. |
| 6,853,863 B2 | 2/2005 | Carter et al. |
| 6,895,280 B2 | 5/2005 | Meadows et al. |
| 6,909,917 B2 | 6/2005 | Woods et al. |
| 7,035,690 B2 | 4/2006 | Goetz |
| 7,127,297 B2 | 10/2006 | Law et al. |
| 7,174,210 B1 | 2/2007 | Levine |
| 7,180,760 B2 | 2/2007 | Varrichio et al. |
| 7,216,001 B2 | 5/2007 | Hacker et al. |
| 7,251,529 B2 | 7/2007 | Greenwood-Van Meerveld |
| 7,271,663 B2 | 9/2007 | Baum et al. |
| 7,317,948 B1 | 1/2008 | King et al. |
| 7,386,348 B2 | 6/2008 | North et al. |
| 7,387,603 B2 | 6/2008 | Gross et al. |
| 7,389,147 B2 | 6/2008 | Wahlstrand et al. |
| 7,463,928 B2 | 12/2008 | Lee et al. |
| 7,477,723 B2 | 1/2009 | Kamegawa et al. |
| 7,505,809 B2 | 3/2009 | Strommer et al. |
| 7,519,428 B1 | 4/2009 | Palmer |
| 7,519,431 B2 | 4/2009 | Goetz et al. |
| 7,522,962 B1 | 4/2009 | Doron et al. |
| 7,526,341 B2 | 4/2009 | Goetz et al. |
| 7,567,834 B2 | 7/2009 | Clayton et al. |
| 7,571,007 B2 | 8/2009 | Erickson et al. |
| 7,623,918 B2 | 11/2009 | Goetz |
| 7,768,151 B2 | 8/2010 | Andreu et al. |
| 7,974,697 B2 | 7/2011 | Maschino et al. |
| 8,055,337 B2 | 11/2011 | Moffitt et al. |
| 8,560,080 B2 | 10/2013 | Goetz et al. |
| 8,738,145 B2 | 5/2014 | Goetz et al. |
| 8,825,169 B2 | 9/2014 | Zhu et al. |
| 8,996,123 B2 | 3/2015 | Goetz et al. |
| 9,358,390 B2 | 6/2016 | Polefko et al. |
| 9,913,975 B2 | 3/2018 | Carbunaru et al. |
| 10,199,125 B2 * | 2/2019 | Rao ............... A61N 1/37211 |
| 2004/0059395 A1 | 3/2004 | North et al. |
| 2004/0098063 A1 | 5/2004 | Goetz |
| 2004/0210273 A1 | 10/2004 | Wang |
| 2004/0267330 A1 | 12/2004 | Lee et al. |
| 2005/0065556 A1 | 3/2005 | Reghabi et al. |
| 2005/0131464 A1 | 6/2005 | Heinrich et al. |
| 2006/0178706 A1 | 8/2006 | Lisogurski et al. |
| 2006/0195145 A1 | 8/2006 | Lee et al. |
| 2006/0229687 A1 | 10/2006 | Goetz et al. |
| 2006/0241720 A1 | 10/2006 | Woods et al. |
| 2006/0259079 A1 | 11/2006 | King |
| 2006/0259099 A1 | 11/2006 | Goetz et al. |
| 2006/0293609 A1 | 12/2006 | Stahmann et al. |
| 2007/0100408 A1 | 5/2007 | Gerber et al. |
| 2007/0203537 A1 | 8/2007 | Goetz et al. |
| 2007/0203540 A1 | 8/2007 | Goetz et al. |
| 2007/0203541 A1 | 8/2007 | Goetz et al. |
| 2007/0203542 A1 | 8/2007 | Goetz et al. |
| 2007/0203544 A1 | 8/2007 | Goetz et al. |
| 2007/0203546 A1 | 8/2007 | Stone et al. |
| 2008/0004674 A1 | 1/2008 | King et al. |
| 2008/0046036 A1 | 2/2008 | King et al. |
| 2008/0071324 A1 | 3/2008 | Miesel et al. |
| 2008/0082137 A1 | 4/2008 | Kieval et al. |
| 2008/0109048 A1 | 5/2008 | Moffitt |
| 2008/0154340 A1 | 6/2008 | Goetz et al. |
| 2008/0163097 A1 | 7/2008 | Goetz et al. |
| 2008/0183256 A1 | 7/2008 | Keacher |
| 2008/0215118 A1 | 9/2008 | Goetz et al. |
| 2008/0215119 A1 | 9/2008 | Woods et al. |
| 2008/0221637 A1 | 9/2008 | Woods et al. |
| 2008/0288023 A1 | 11/2008 | John |
| 2008/0294211 A1 | 11/2008 | Moffitt |
| 2009/0018617 A1 | 1/2009 | Skelton et al. |
| 2009/0024189 A1 | 1/2009 | Lee et al. |
| 2009/0149917 A1 | 6/2009 | Whitehurst et al. |
| 2010/0023069 A1 | 1/2010 | Moffitt et al. |
| 2010/0023070 A1 | 1/2010 | Moffitt et al. |
| 2010/0106219 A1 | 4/2010 | Torgerson et al. |
| 2010/0121409 A1 | 5/2010 | Kothandaraman et al. |
| 2011/0093044 A1 | 4/2011 | Moffitt |
| 2011/0313268 A1 | 12/2011 | Kokones et al. |
| 2013/0131760 A1 | 5/2013 | Rao et al. |
| 2016/0082261 A1 | 3/2016 | Moffit et al. |
| 2016/0158564 A1 | 6/2016 | Rao et al. |
| 2017/0165490 A1 | 6/2017 | Wechter |
| 2017/0333718 A1 | 11/2017 | Moffitt et al. |

FOREIGN PATENT DOCUMENTS

| | | |
|---|---|---|
| WO | 2009076211 A1 | 6/2009 |
| WO | 2009134480 A1 | 11/2009 |
| WO | 2009137121 A1 | 11/2009 |
| WO | 2010011721 A1 | 1/2010 |

OTHER PUBLICATIONS

Bourret et al., "Programmable High-Amplitude Balanced Stimulus Current-Source for Implantable Microstimulators," Proceedings of the 19th Annual International Conference of the IEEE Engineering in Medicine and Biology Society, Oct. 30-Nov. 2, 1997, pp. 1938-1941.

Kim et al., "A 64-Site Multishank CMOS Low-Profile Neural Stimulating Probe," IEEE Journal of Solid State Circuits, vol. 31, No. 9, Sep. 1996, pp. 1230-1238.

Lee et al., "AIM Targeting Technique: A Novel Method of Focusing the Volume of Activation on the Dorsal Column with Multiple Independent Current Control in a Computational Model," Boston Scientific Neuromodulation, Valencia, California, presented at 13th North American Neuromodulation Society Annual Meeting, Las Vegas, Nevada, Dec. 3-6, 2009, Poster ID A107, 2 pp.

St-Amand et al., "Design and Optimization of a Low DC Offset CMOS Current-Source Dedicated to Implantable Miniaturized Stimulators," Analog Integrated Circuits and Signal Processing, vol. 11, Applicant points out, in accordance with MPEP 609.04(a), that the year of publication, 1996, is sufficiently earlier than the effective U.S. filing date, so that the particular month of publication is not in issue, pp. 47-61.

Prosecution History from U.S. Appl. No. 12/906,418, dated Oct. 18, 2010 through Dec. 23, 2014, 182 pp.

International Search Report and Written Opinion of International Application No. PCT/US2020/062053, dated Feb. 19, 2021, 15 pp.

* cited by examiner

INDEPENDENT CONTROL OF ELECTRICAL STIMULATION AMPLITUDE FOR ELECTRODES FOR DELIVERY OF ELECTRICAL STIMULATION THERAPY

TECHNICAL FIELD

The disclosure relates to medical devices and, more particularly, to medical devices that deliver electrical stimulation therapy.

BACKGROUND

Medical devices may be used to treat a variety of medical conditions. Medical electrical stimulation devices, for example, may deliver electrical stimulation therapy to a patient via electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. The electrical stimulation device may comprise a leadless stimulator. In some cases, implantable electrodes may be coupled to an external electrical stimulation generator via one or more percutaneous leads or fully implanted leads.

Medical electrical stimulators may be used to deliver electrical stimulation therapy to patients to relieve a variety of symptoms or conditions such as chronic pain, tremor, Parkinson's disease, depression, epilepsy, urinary or fecal incontinence, pelvic pain, sexual dysfunction, obesity, or gastroparesis. An electrical stimulator may be configured to deliver electrical stimulation therapy via leads that include electrodes proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

SUMMARY

In general, this disclosure describes programming techniques for medical devices that deliver electrical stimulation. In particular, this disclosure describes a user interface that is able to receive, as user input, a desired amplitude for individual stimulation pulses that are to be delivered to a particular electrode in an electrical stimulation system. In addition, this disclosure describes programming techniques for utilizing such user input defining a desired amplitude to determine parameters of an electrical stimulator that achieve the desired amplitude. In accordance with various techniques of this disclosure, the electrical stimulator achieves the desired amplitude while maintaining the amplitude of other stimulation pulses delivered to one or more other electrodes.

To illustrate, an example electrical stimulator includes a master power source having an adjustable master amplitude and a stimulation generator coupled to multiple electrodes. The stimulation generator delivers electrical stimulation pulses to electrodes at various amplitudes specified by the user. In some examples, the master power source may include a master voltage amplitude and/or a master current amplitude used to achieve individual amplitudes for individual electrodes. In examples involving a master electrical current amplitude, the stimulation generator includes, for each electrode, a finite number of individually controllable current regulator branches. In this way, by selectively activating some or all of the current regulator branches, the stimulation generator may deliver electrical stimulation pulses at an electrical current amplitude that is a fraction of the master electrical current amplitude. In such examples, a fraction is defined as the particular number of regulator branches activated at that time for a particular electrode compared to a total number of regulator branches available.

In an illustrative example, the stimulation generator may deliver, to a first electrode, stimulation pulses having a first electrical current amplitude that is a first fraction of the master amplitude. Similarly, the stimulation generator may deliver, to a second electrode, stimulation pulses having a second electrical current amplitude that is a second fraction of the master amplitude, which in some instances, may be equivalent to the first fraction. In this example, the stimulation generator may increase or decrease the electrical current amplitude delivered to an adjustment-targeted electrode by either activating more or less current regulator branches that correspond to the adjustment-targeted electrode, by increasing the master amplitude, or some combination of the two.

In some instances, where a desired electrical current amplitude for a particular electrode exceeds the master electrical current amplitude, the stimulation generator may adjust the master electrical current amplitude, up to a maximum electrical current amplitude available from the master current source. In some examples, however, the user may only want to affect the electrical current amplitude for one electrode and not affect the electrical current amplitude for other electrodes, which may happen when the master electrical current amplitude is increased without any changes to electrode fractions. Thus, in order to maintain the stimulation pulses delivered to other electrodes at previously defined current amplitudes, the stimulation generator may adjust fractions of non-adjustment targeted electrodes. In addition, the electrical stimulator may adjust the master amplitude up to a maximum amplitude available from the particular power source in order to provide a sufficient master amplitude to support the desired electrical current amplitudes for individual stimulation pulses. In any event, a user may request from the electrical stimulation system adjustments, or initial settings, for electrical current amplitudes that may be controlled from a user interface. As such, the user interface receives, as user input, a desired electrical current amplitude for an electrode targeted for adjustment.

In this way, processing circuitry of the electrical stimulator may cause an adjustment to a first electrical current amplitude, while maintaining the electrical current amplitudes of other electrodes as close to the original electrical current amplitude. That is, a single user input of one desired electrical current amplitude for a particular electrode targeted for adjustment, whether setting the amplitude anew or adjusting a previously set amplitude, may result in an implementation of the desired electrical current amplitude. The desired electrical current amplitude may be implemented regardless of whether the desired current amplitude is greater than, less than, or equal to a master electrical current amplitude, while simultaneously maintaining the electrical current amplitude delivered to other electrodes not targeted for adjustment by adjusting the number of current regulator branches corresponding to the non-adjustment targeted electrodes.

In one example, this disclosure is directed to a neuromodulation system comprising: a first electrode; a second electrode; a stimulation generator configured to deliver first stimulation pulses to the first electrode and second stimulation pulses to the second electrode, wherein a first electrical current amplitude of the first stimulation pulses is a first fraction of a master amplitude and a second electrical current amplitude of the second stimulation pulses is a second fraction of the master amplitude. The neuromodulation system further comprises a processor configured to generate an initial instruction for the stimulation generator to deliver: (i) the first simulation pulses based on the first fraction of the master amplitude, and (ii) the second stimulation pulses based on the second fraction of the master amplitude. The processor is further configured to receive user input comprising a desired electrical current amplitude; and determine that an adjustment to the first electrical current amplitude of the first stimulation pulses is required based on the desired electrical current amplitude. The processor is further configured to determine, based at least in part on a comparison of the desired electrical current amplitude to the master amplitude, a target adjustment. The processor is further configured to: (A) determine, as the target adjustment, an adjustment to at least the first fraction, or (B) determine, as the target adjustment: (i) an adjustment to the master amplitude, and (ii) an adjustment to at least the second fraction relative to the master amplitude adjustment. The processor is further configured to generate, based at least in part on the target adjustment, an adjustment instruction for the stimulation generator to deliver the first stimulation pulses at the desired electrical current amplitude and deliver the second stimulation pulses at approximately the same second electrical current amplitude.

In another example, the disclosure is directed to a method that comprises: generating an initial instruction for a stimulation generator to deliver: (i) first simulation pulses based on a first fraction of a master amplitude, and (ii) second stimulation pulses based on a second fraction of the master amplitude; and receiving user input comprising a desired electrical current amplitude. The method further comprises determining that an adjustment to the first electrical current amplitude of the first stimulation pulses is required based on the desired electrical current amplitude. The method further comprises determining, based at least in part on a comparison of the desired electrical current amplitude to the master amplitude, a target adjustment. The method further comprises (A) determining, as the target adjustment, an adjustment to at least the first fraction, or (B) determining, as the target adjustment: (i) an adjustment to the master amplitude, and (ii) an adjustment to at least the second fraction relative to the master amplitude adjustment. The method further comprises generating, based at least in part on the target adjustment, an adjustment instruction for the stimulation generator to deliver the first stimulation pulses at the desired electrical current amplitude and deliver the second stimulation pulses at approximately the same second electrical current amplitude.

In another example, the disclosure is directed to a computer-readable storage medium including instructions that, when executed, cause at least one processor to at least: generate an initial instruction for a stimulation generator to deliver: (i) first simulation pulses based on a first fraction of a master amplitude, and (ii) second stimulation pulses based on a second fraction of the master amplitude; and receive user input comprising a desired electrical current amplitude. The instructions, when executed, further cause the at least one processor to at least: determine that an adjustment to the first electrical current amplitude of the first stimulation pulses is required based on the desired electrical current amplitude. The instructions, when executed, further cause the at least one processor to at least: determine, based at least in part on a comparison of the desired electrical current amplitude to the master amplitude, a target adjustment, the target adjustment comprising: (i) adjustment to at least the first fraction, or (ii) an adjustment to the master amplitude and an adjustment to at least the second fraction relative to the adjustment to the master amplitude. The instructions, when executed, further cause the at least one processor to at least: generate, based at least in part on the target adjustment, an adjustment instruction for the stimulation generator to deliver the first stimulation pulses at the desired electrical current amplitude and deliver the second stimulation pulses at approximately the same second electrical current amplitude.

The details of one or more aspects of the disclosure are set forth in the accompanying drawings and the description below. Other features, objects, and advantages will be apparent from the description and drawings, and from the claims.

DETAILED DESCRIPTION

This disclosure describes various techniques for medical devices to deliver electrical stimulation therapy using electrodes and electrical stimulation pulses having stimulation amplitudes defined by an electrical current amplitude. The medical devices may receive user input of the electrical current amplitude from a programmer, via a user interface. The user input may specify changes in current amplitudes for stimulation pulses delivered by electrodes of one or more leads. Responsive to the user input, processing circuitry of an electrical stimulation generator may determine whether to implement at least one of a first fraction adjustment or a second fraction adjustment as a target adjustment. That is, in an example involving at least two electrodes, the target adjustment may achieve the desired electrical current amplitude by adjusting a first fraction of an adjustment electrode or adjusting a master electrical current amplitude, along with adjusting at least one second fraction of a non-adjustment electrodes or non-adjustment electrodes, in accordance with various techniques of this disclosure.

Figure 1:
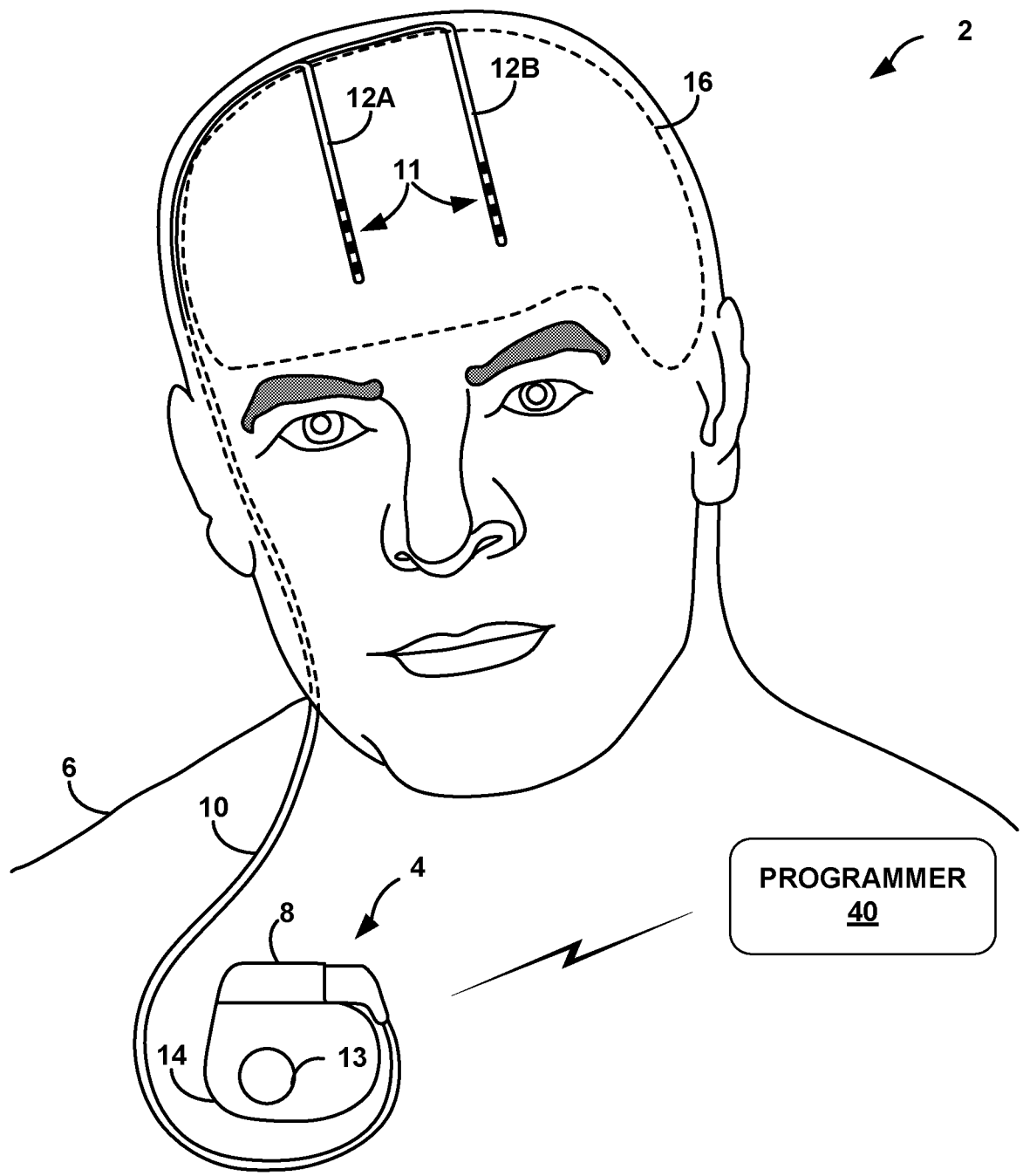
FIG. 1 is a conceptual diagram illustrating an example therapy system that includes an electrical stimulator coupled to a stimulation lead, in accordance with various techniques of this disclosure.

FIG. 1 is a conceptual diagram illustrating an example system 2 that may be used to deliver stimulation therapy to patient 6. Patient 6 ordinarily, but not necessarily, will be a human. Generally, therapy system 2 includes electrical stimulator 4 (e.g., an implantable medical device (IMD)) that delivers electrical stimulation to patient 6 via one or more electrodes. Electrical stimulator 4 may include a master current and a current regulator array allowing electrical stimulator 4 to regulate current sourced or sunk by one or more electrodes 11. As such, electrical stimulator 4 may include a number of current regulator branches that may be used to implement a current regulator for one or more electrodes 11. For purposes of description the electrodes are described as being implantable electrodes. However, the example techniques are not limited to implantable electrodes.

The electrodes may be deployed on one or more medical leads, such as implantable medical lead 10, and in some cases on a housing electrode. The electrical stimulation may be in the form of controlled current pulses or voltage pulses, or substantially continuous current or voltage waveforms. A stimulation program may define various parameters of the pulses or waveforms. The pulses or waveforms may be delivered substantially continuously or in bursts, segments, or patterns, and may be delivered alone or in combination with pulses or waveforms defined by one or more other stimulation programs. In some examples, one or more of the electrodes may be located on a housing 14 of the electrical stimulator 4. In addition, implantable electrodes may be deployed on a leadless stimulator.

In some examples, electrical stimulator 4 may deliver, for example, deep brain stimulation (DBS) or cortical stimulation (CS) therapy to patient 6 via the electrodes carried by lead segments 12. Although FIG. 1 shows a particular stimulation environment (e.g., DBS), the techniques of this disclosure are not so limited, and electrical stimulator 4 may deliver stimulation therapy to other parts of patient 6, such as the spinal cord of patient 6 as described in U.S. Pat. No. 8,560,080, entitled, "PROGRAMMING TECHNIQUES FOR CONTROLLING RATE OF CHANGE OF ELECTRICAL STIMULATION THERAPY," by Goetz et al, and U.S. Pat. No. 8,996,123, entitled, "MANAGING ELECTRICAL STIMULATION THERAPY BASED ON VARIABLE ELECTRODE COMBINATIONS," by Goetz et al, the contents of which are incorporated by reference herein in their entirety. For example, other electrical stimulation systems may be configured to deliver electrical stimulation to gastrointestinal organs, pelvic nerves or muscle, peripheral nerves, or other stimulation sites. In addition, although FIG. 1 shows a fully implantable electrical stimulator 4, techniques described in this disclosure may be applied to external stimulators having electrodes deployed via percutaneous leads.

In the example illustrated in FIG. 1, electrical stimulator 4 is implanted in a clavicle region of patient 6. Electrical stimulator 4 generates programmable electrical stimulation (e.g., a current or voltage waveform or current or voltage pulses) and delivers the stimulation via a medical lead 10 carrying an array of stimulation electrodes 11. In general, delivery of electrical stimulation using controlled current pulses will be described in this disclosure for purposes of illustration. In some cases, electrical stimulator may include multiple leads. In the example of FIG. 1, a distal end of lead 10 is bifurcated and includes two lead segments 12A and 12B (collectively "lead segments 12"). Lead segments 12A and 12B each include a set of electrodes forming part of the array of electrodes 11. In various examples, lead segments 12A and 12B may each carry four, eight, or sixteen electrodes. In FIG. 1, each lead segment 12A, 12B carries four electrodes, configured as ring electrodes at different axial positions near the distal ends of the lead segments 12. Throughout the remainder of this disclosure, for purposes of simplicity, the disclosure may generally refer to electrodes carried on "leads" which may be "lead segments" or the entire lead.

FIG. 1 further depicts a housing electrode 13. Housing electrode 13 may be formed integrally with an outer surface of hermetically-sealed housing 14 of electrical stimulator 4, or otherwise coupled to housing 14. In one example, housing electrode 13 may be described as an active, non-detachable electrode on electrical stimulator 4. In some examples, housing electrode 13 is defined by an uninsulated portion of an outward facing portion of housing 14 of electrical stimulator 4. Other divisions between insulated and uninsulated portions of housing 14 may be employed to define two or more housing electrodes. In some examples, housing electrode 13 comprises substantially all of housing 14, one side of housing 14, a portion of housing 14, or multiple portions of housing 14. In one example implementation of the techniques of this disclosure, e.g., an omnipolar arrangement, one or more electrodes 11 may transfer stimulation pulses from lead 10 to patient 6 substantially simultaneously with stimulation pulses delivered via housing electrode 13.

In some examples, electrical stimulator 4 may be coupled to one or more leads which may or may not be bifurcated. In such examples, the leads may be coupled to electrical stimulator 4 via a common lead extension or via separate lead extensions. A proximal end of lead 10 may be coupled to a header on electrical stimulator 4. Conductors in the lead body may electrically connect stimulation electrodes located on lead segments 12 to electrical stimulator 4. Lead 10 traverses from the implant site of electrical stimulator 4 along the neck of patient 6 to the brain 16 of patient 6. In some examples, lead segments 12A and 12B may be implanted within the right and left hemispheres, respectively, in order to deliver electrical stimulation to one more regions of brain 16.

Lead segments 12A, 12B may be implanted within a desired location of brain 16 through respective holes in the cranium of patient 6. Lead segments 12A, 12B may be placed at any location within brain 16 such that the electrodes located on lead segments 12A, 12B are capable of providing electrical stimulation to targeted tissue. The electrodes of lead segments 12A, 12B are shown as ring electrodes. In some examples, the electrodes of lead segments 12A, 12B may have different configurations. For example, the electrodes of lead segments 12A, 12B may have a complex electrode array geometry that is capable of producing shaped electrical fields. The complex electrode array geometry may include multiple electrodes (e.g., partial ring or segmented electrodes) around the perimeter of each lead segments 12A, 12B. In some examples, lead segments 12 may have shapes other than elongated cylinders as shown in FIG. 1. For example, lead segments 12 may be paddle leads, spherical leads, bendable leads, or any other type of shape effective in treating patient 6. In addition, the electrodes may be electrode pads on a paddle lead, circular electrodes surrounding the body of a lead, conformable electrodes, cuff electrodes, segmented electrodes, or any other type of electrodes capable of forming unipolar, bipolar, multi-polar, etc. electrode configurations.

Therapy system 2 may include a programmer 40, such as an external programmer operated by a clinician or patient. In some examples, a programmer 40 may be a handheld computing device that permits a clinician to program stimulation therapy for patient 6 via a user interface. For example, using programmer 40, the clinician may specify stimulation parameters for use in delivery of stimulation therapy. Programmer 40 may support telemetry with electrical stimulator 4 to download programs and, optionally, upload operational or physiological data stored by electrical stimulator 4. Programmer 40 may also include a display and input keys to allow patient 6 or a clinician to interact with programmer 40 and electrical stimulator 4. In this manner, programmer 40 provides patient 6 with a user interface for control of the stimulation therapy delivered by electrical stimulator 4. For example, patient 6 may use programmer 40 to start, stop or adjust electrical stimulation. In particular, programmer 40 may permit patient 6 to adjust stimulation parameters of a program, such as duration, current or voltage amplitude, pulse width, pulse shape, and pulse rate. Patient 6 may also select a program (e.g., from among a plurality of stored programs) as the present program to control delivery of stimulation by electrical stimulator 4.

In some cases, programmer 40 may be characterized as a physician or clinician programmer 40. For example, programmer 40 may include a clinician programmer if programmer 40 is primarily intended for use by a physician or clinician. In other cases, programmer 40 may be characterized as a patient programmer if programmer 40 is primarily intended for use by a patient. In general, a physician or clinician programmer may support selection and generation of programs by a clinician for use by stimulator 4, whereas a patient programmer may support adjustment and selection of such programs by a patient during ordinary use.

Whether programmer 40 is configured for clinician or patient use, programmer 40 may communicate with electrical stimulator 4 or any other computing device via wireless communication. Programmer 40, for example, may communicate via wireless communication with electrical stimulator 4 using RF telemetry techniques known in the art. Programmer 40 may also communicate with another programmer or computing device via a wired or wireless connection using any of a variety of local wireless communication techniques, such as radio frequency (RF) communication according to the 802.11 or Bluetooth specification sets, infrared communication according to the Infrared Data Association (IrDA) specification set, or other standard or proprietary telemetry protocols. Programmer 40 may also communicate with another programming or computing device via exchange of removable media, such as magnetic or optical disks, or memory cards or sticks. Further, programmer 40 may communicate with electrical stimulator 4 and other programming devices via remote telemetry techniques known in the art, communicating via a local area network (LAN), wide area network (WAN), public switched telephone network (PSTN), or cellular telephone network, for example.

In some examples, electrical stimulator 4 delivers stimulation according to a group of programs at a given time. Each program of such a program group may include respective values for each of a plurality of therapy parameters, such as respective values for each of current or voltage amplitude, pulse width, pulse shape, pulse rate and electrode configuration (e.g., electrode combination and polarity). Electrical stimulator 4 may interleave pulses or other signals according to the different programs of a program group. In such examples, programmer 40 may be used to create programs, and assemble the programs into program groups. In some examples, programmer 40 may be used to adjust stimulation parameters of one or more programs of a program group, and select a program group as the current program group to control delivery of stimulation by electrical stimulator 4.

Generally, system 2 delivers stimulation therapy to patient 6 in the form of constant current or voltage waveforms or constant current or voltage pulses. The shapes of the pulses may vary according to different design objectives, and may include ramped or trapezoidal pulses, sinusoidal or otherwise curved pulses, stepped pulses having two or more discrete amplitudes, closely spaced pairs of pulses, and biphasic (positive and negative aspects within a single pulse) or monophasic (only positive or only negative aspects within a single pulse) variations of any of the above. In the case of current-based stimulation, electrical stimulator 4 regulates current that is sourced or sunk by one or more electrodes, referred to as regulated electrodes. In some examples, one or more of the electrodes may be unregulated. In such configurations, the housing electrode and/or a lead electrode may be the unregulated electrode.

A source current may refer to a positive current that flows out of an electrode (anode), whereas a sink current may refer to a negative current that flows into an electrode (cathode). Regulated source currents may sum to produce a greater overall source current (e.g., currents from a plurality of source currents sum together to generate the overall source current). Likewise, regulated sink currents may sum to produce a greater overall sink current (e.g., currents from a plurality of sink currents sum together to generate the overall ink current). Regulated source and regulated sink currents may partially or entirely cancel one another, producing a net difference in the form of a net source current or sink current in the case of partial cancellation. In some examples, an unregulated current path can source or sink current approximately equal to this net difference. In some examples, regulated source and sink currents may be substantially balanced.

As mentioned above, in some example implementations (e.g., omnipolar arrangements), one or more electrodes 11 may transfer stimulation current from lead 10 to the tissue substantially simultaneously with stimulation current delivered to patient 6 from housing electrode 13. In some example implementations (e.g., bipolar/multipolar arrangements), one or more electrodes 11 may be configured to act as anodes and source current while one or more different electrodes 11 may be configured to act as cathodes and sink current. In another example implementation (e.g., unipolar arrangements), housing electrode 13 may be configured to act as an anode and source current while one or more electrodes 11 on one or more leads are configured to act as cathodes and sink current. Techniques of this disclosure may be implemented using unipolar arrangements, bipolar/multipolar arrangements, and omnipolar arrangements.

A user, such as a clinician or patient 6, may interact with a user interface of programmer 40 to program electrical stimulator 4. In accordance with various techniques described in this disclosure, programmer 40 may be used to receive user input, via the user interface indicating a desired electrical current amplitude. Programmer 40 may control electrical stimulator 4 to cause electrical stimulator 4 to deliver stimulation pulses to electrodes at the desired electrical current amplitudes, as described in more detail below, or otherwise program stimulator 4. Programming of electrical stimulator 4 may refer generally to the generation and transfer of commands, programs, or other information to control the operation of electrical stimulator 4. For example, programmer 40 may transmit programs, parameter adjustments, program selections, group selections, or other information to control the operation of electrical stimulator 4. In addition, programming of stimulator 4 may include receiving, via programmer 40, user input indicating a target stimulation zone and controlling the electrical stimulator to transition electrical stimulation from an initial stimulation zone to the target stimulation zone via a sequence of one or more intermediate stimulation zones.

Electrical stimulator 4 and programmer 40 may communicate via cables or a wireless communication, as shown in FIG. 1. Programmer 40 may, for example, communicate via wireless communication with electrical stimulator 4 using RF telemetry techniques. Programmer 40 may also communicate with other programmers using any of a variety of local wireless communication techniques, such as RF communication according to the 802.11 or Bluetooth™ specification sets, infrared communication (e.g., according to the IrDA standard), or other standard or proprietary telemetry protocols. Programmer 40 may include a transceiver to permit bi-directional communication with electrical stimulator 4.

In some examples, processing circuitry of programmer 40 may receive user input via a user interface that allows a user (e.g., clinician, physician, patient, etc.) to input electrical current amplitude values defining desired current amplitudes for electrical stimulation pulses delivered to one or more electrodes 11. In an illustrative example, the user interface may accept as input '1.2' milliamps (mA; also, milliamperes) with respect to a first electrode 11. In this example, the input of '1.2' indicates a user command for the first electrode to deliver a stimulation pulse having an electrical current amplitude of 1.2 mA or a stimulation pulse that approximates 1.2 mA (e.g., 1.19 mA) and that in any event would be displayed as 1.2 mA on the user interface due to a rounding of the actual current amplitude value. For example, an electrical current amplitude of a stimulation pulse delivered to a first electrode 11 may be achieved by activating or deactivating a number of current regulator branches that regulate a master current. In the illustrative example, processing circuitry of electrical stimulator 4, or processing circuitry of a stimulation generator, may perform various adjustments, such as by adjusting fraction values that define a number of current regulator branches of the stimulation system relative to a total number of current regulator branches and/or by adjusting master electrical current amplitudes, to achieve the desired electrical current amplitude of 1.2 mA.

The user interface of programmer 40 may display the electrical current amplitude corresponding to each electrode. In some instances, the user interface of programmer 40 may also display the fractional amount associated with each electrical current amplitude for one or more electrodes. In any event, the user may adjust the current amplitude corresponding to a particular electrode by increasing or decreasing the electrical current amplitude value displayed on the user interface of programmer 40.

In an example involving a user adjusting fraction contributions, a clinician, when attempting to adjust a current amplitude for a particular electrode, adjusts the contribution of the electrode by defining the degree to which a given electrode delivers a desired intensity relative to a master current. The clinician may set a contribution for a particular electrode on a scale of 0.0 (0%) to 1.0 (100%), where the percentages or decimal values indicate a fraction of a total number of current regulator branches the stimulation generator is to use to implement a current regulator associated with the particular electrode.

In some examples, a user interface of programmer 40 may display the electrical current amplitude corresponding to each electrode. The user interface may provide fillable fields, or other adjustment input devices, such as increase or decrease input keys, that allow a user to input a desired electrical current amplitude for a given electrode 11 targeted for adjustment, or for multiple electrodes 11 targeted for adjustment, of electrical stimulator 4. The processing circuitry of an electrical stimulator 4 may receive as user input a desired electrical current amplitude or an adjustment to an electrical current amplitude. The desired electrical current amplitude may be inputted in the form of amperes (e.g., milliamperes).

The desired electrical current amplitude may be more, less, or equal to a current amplitude setting of a master electrical current amplitude. That is, the value included with the user input may be compared directly to the master electrical current amplitude. The master electrical current amplitude defines the maximum electrical current amplitude for any given electrode 11 of the stimulation system. The master electrical current amplitude provides source power to electrodes 11 based on a number of current regulator branches activated for each electrode 11. In one example, a first electrode may have 64 of 64 branches activated (e.g., 64/64), and thus, will provide 100% of the master amplitude, whereas a second electrode may have 32 out of 64 branches activated (e.g., 32/64), and thus, will provide 50% of the master amplitude. The master amplitude may be adjusted upward or downward as needed, up to a maximum master amplitude, in which case, the number of branches for the electrodes may need to be adjusted based on whether the electrode is an electrode for adjustment or an electrode that is intended to maintain a constant electrical current amplitude.

Based on the desired electrical current amplitude or the adjustment to the electrical current amplitude, the processing circuitry of electrical stimulator 4 may adjust various fractions and/or master current amplitudes. In an example including at least two electrodes, the processing circuitry of electrical stimulator 4 may perform one of two fraction adjustments, including an adjustment to a first fraction of an electrode targeted for an amplitude adjustment (hereinafter, "first fraction adjustment") or an adjustment to a master electrical current amplitude and an adjustment to a second fraction corresponding to another electrode not targeted for an amplitude adjustment (hereinafter, "second fraction adjustment"). While this disclosure references two or three electrodes in some instances for illustrative purposes, the techniques of this disclosure are not so limited, and the fraction adjustments may apply to any number of electrodes used to provide electrical stimulation using a master or reference amplitude.

Figure 2:
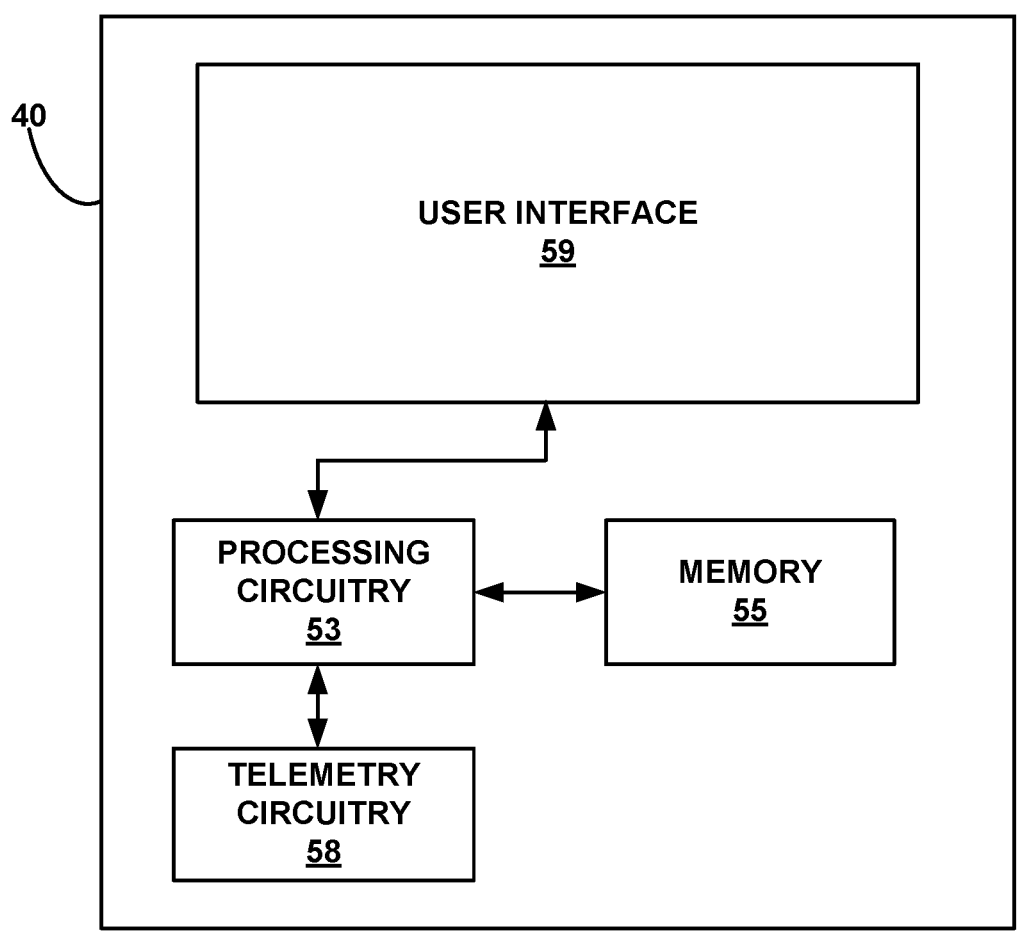
FIG. 2 is a block diagram illustrating various example components of a programmer, such as the programmer in FIG. 1, for use with an electrical stimulator, in accordance with various techniques of this disclosure.

FIG. 2 is a functional block diagram illustrating various components of programmer 40 for an electrical stimulator 4. As shown in FIG. 2, programmer 40 includes processing circuitry 53, memory 55, telemetry circuitry 58, and user interface 59. In general, processing circuitry 53 controls user interface 59, stores and retrieves data to and from memory 55, and controls transmission of data with electrical stimulator 4 through telemetry circuitry 58. Processing circuitry 53 may take the form of one or more microprocessors, controllers, digital signal processors (DSPs), application-specific integrated circuits (ASICs), field-programmable gate arrays (FPGAs), or equivalent discrete or integrated logic circuitry. The functions attributed to processing circuitry 53 herein may be embodied as software, firmware, hardware or any combination thereof.

Memory 55 may store instructions that cause processing circuitry 53 to provide various aspects of the functionality ascribed to programmer 40 herein. Memory 55 may include any fixed or removable magnetic, optical, or electrical media, such as random access memory (RAM), read-only memory (ROM), compact disc ROM (CD-ROM), magnetic memory, electronically-erasable programmable ROM (EE- PROM), non-volatile random access memory (NVRAM), flash memory, etc. Memory 55 may also include a removable memory portion that may be used to provide memory updates or increases in memory capacities. A removable memory may also allow patient data to be easily transferred from programmer 40 to another computing device. Memory 55 may also store information that controls operation of electrical stimulator 4.

Telemetry circuitry 58 allows the transfer of data to and from electrical stimulator 4. Telemetry circuitry 58 may communicate automatically with electrical stimulator 4 at a scheduled time or when telemetry circuitry 58 detects the proximity of electrical stimulator 4. Alternatively, telemetry circuitry 58 may communicate with electrical stimulator 4 when signaled by a user through user interface 59. To support RF communication, telemetry circuitry 58 may include appropriate electronic components, such as amplifiers, filters, mixers, encoders, decoders, etc.

In some examples, programmer 40 may communicate wirelessly with electrical stimulator 4 using, for example, RF communication or proximal inductive interaction. This wireless communication is possible through the use of telemetry circuitry 58 which may be coupled to an antenna. Programmer 40 may also be configured to communicate with another computing device via wireless communication techniques, or direct communication through a wired, e.g., network, connection. Examples of local wireless communication techniques that may be employed to facilitate communication between programmer 24 and another computing device include RF communication based on the 802.11 or Bluetooth specification sets, infrared communication.

Programmer 40 may include a user interface 59. As mentioned above, a user (e.g., a clinician or patient 6) may interact with user interface 59 in order to, for example, manually select, change or modify programs, adjust voltage or current amplitude of stimulation pulses delivered by specific electrodes or a plurality of electrodes, or view stimulation data. User interface 59 may include a screen and one or more input buttons or input fields that allow programmer 40 to receive input from a user. The screen may be a liquid crystal display (LCD), plasma display, dot matrix display, or touch screen. The input buttons may include a touch pad, increase or decrease buttons/keys, and other input media needed to control electrical stimulation. An example of user interface 59 is described with reference to FIG. 3 below.

User interface 59 may receive, as user input, a desired electrical current amplitude for a first electrode. In some examples, a user may input, via user interface 59, a desired electrical current amplitude value for electrodes 11. In some examples, the user input may include an initial setting for one or more electrodes 11 or may include an adjustment to an electrode already having a programmed electrical current amplitude setting. Processing circuitry 53 may receive the user input comprising the desired electrical current amplitude for a particular electrode of a multiple electrode system and may transmit instructions (e.g., adjustment instructions) to electrical stimulator 4 to implement adjustments to the electrical stimulator 4 to deliver electrical stimulation in accordance with the desired electrical current amplitude. In another example, processing circuitry 53 may transmit the user input to electrical stimulator 4, via telemetry circuitry 58, where electrical stimulator 4 may then determine a target adjustment and generate adjustment instructions. As such, telemetry circuitry 58 may communicate milliamp values to electrical stimulator 4 as adjustment instructions based on the user input defining a desired electrical current value. In another example, telemetry circuitry 58 may communicate fractional values to electrical stimulator 4 as adjustment instructions, where the adjustment instructions indicate to electrical stimulator 4 a configuration for the regulator branches based on the user input defining a desired electrical current value.

In some examples, programmer 40 may determine an adjustment for the electrical stimulator based on the user input comprising the desired electrical current amplitude. The adjustment may be selected from one of a first fraction adjustment or a second fraction adjustment depending on whether or not the desired electrical current amplitude for an electrode is greater than, equal to, or less than the master electrical current amplitude, and in some instances whether the fraction for a particular electrode targeted for adjustment is at a fraction maximum, such as in an example including segmented electrode rings.

When adjustments cause changes in the master electrical current amplitude, in order to maintain the electrical current amplitude of other electrodes not targeted for adjustment, the fraction of the other electrodes may need to be adjusted relative to the change in the master electrical current amplitude. This is because changes to the master electrical current amplitude cause changes to the electrical current amplitudes for other electrodes unless more or less of the master electrical current amplitude is used for the non-adjustment targeted electrodes as defined by changes in a number of current regulator branches activated compared to a total of current regulator branches available. As mentioned, the ratio of current regulator branches activated compared to a total of current regulator branches available is referred to throughout as a fraction of the master amplitude used to obtain individual amplitudes for individual electrodes.

Figure 3:
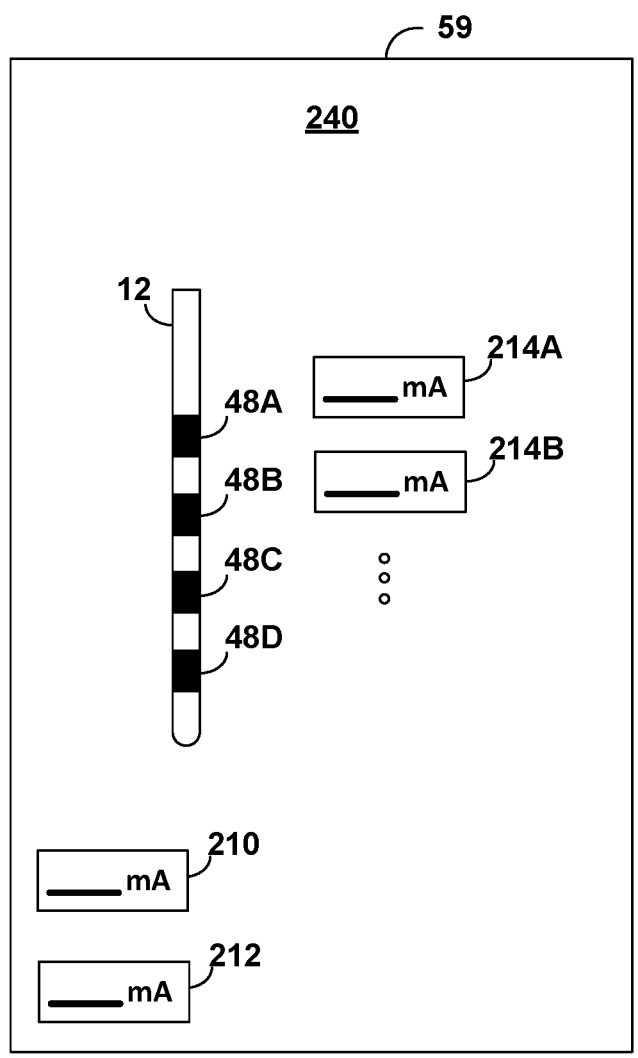
FIG. 3 illustrates an example programmer screen, in accordance with this disclosure.

FIG. 3 illustrates an example screen of user interface 59 presented on programmer 40. User interface 59 may be used to adjust electrical current values of one or more electrodes 48 of one or more leads 12. Electrodes 48 are an example of electrodes 11 of FIG. 1. FIG. 3 depicts display window 240 of user interface 59, which is displaying one example lead 12. In some examples, user interface 59 may display a plurality of leads, each having one or more electrodes 48.

In the example of FIG. 3, window 240 graphically depicts an example lead 12 that may correspond to one of leads 12A or 12B in FIG. 1. In the illustrative example, lead 12 includes four electrodes, namely electrodes 48A-48D (referred to collectively as "electrodes 48"). Lead 12 may have more, or fewer, electrodes 48, depending on the particular lead configuration in use, and more than one lead may be displayed on screen 240, such as lead segments 12A and 12B shown in FIG. 1. For ease of illustration, only four electrodes (or a portion of four electrodes) are depicted on lead 12 and only two electrodes are used to illustrate the various electrical current adjustment examples, in accordance with various techniques of this disclosure. In addition, window 240 may depict stimulation zones, electrical field zones, activation zones, etc. (not shown). For example, a zone may be an anodal zone generated by one or more of electrodes 48 of lead 12 sourcing current. A second zone may be a cathodal zone generated by one or more of electrodes 48 of lead 12 sinking current.

In the example of FIG. 3, adjacent each of the four electrodes, display window 240 may indicate the electrical current associated with each of electrodes 48 or electrode combination. In particular, electrode 48A may include a fillable field or otherwise adjustable field 214A and electrode 48B may include another fillable field or otherwise adjustable field 214B (hereinafter, "fields 214"). Fields 214 may indicate how much electrical current each of electrodes 48 may be sourcing or sinking (e.g., as measured in milliamperes). Although only shown with respect to electrodes 48A and 48B (i.e., example first and second electrodes), fields 214 may apply equally to all electrodes, including segmented electrodes in the case of a segmented lead implementation.

In some examples, display window 240 of user interface 59 may include display windows 210 and 212 indicating information regarding a master electrical current amplitude and/or a maximum current amplitude. In some examples, user interface 59 may provide an option for a user to hide from display window 240 information regarding the master electrical current amplitude and/or the maximum current amplitude. In this way, the user interface may allow the user to focus on adjusting electrical current amplitudes for individual electrodes 48 or combinations of electrodes 48. In any event, windows 210 or 212 may provide the master current amplitude and a maximum current amplitude. In such examples, user interface 59 may alert user as a desired electrical current amplitude approaches a maximum value. That is, user interface 59 may hide from display windows 210 or 212 in favor of displaying the electrical current amplitudes for respective electrodes or electrode combinations.

In an illustrative example, user interface 59 may allow a user to provide user input directly using fields 214 to achieve a desired electrical current amplitude for one or more electrodes 48. For instance, user interface 59 may accept as input '1.1' in field 214A and '1.2' in field 214B. In some instances, one or both fields may be prepopulated with electrical current amplitude values, in which case, the user may adjust the prepopulated values with adjustment values. In one example, user interface 59 may display '1.1 mA' in field 214A, indicating that electrode 48A is programmed with 1.1 mA as the stimulation amplitude. As such, user interface 59 may accept as input an adjustment to first electrode 48A from '1.1' to a higher or lower amplitude value. For example, user interface 59 may accept an adjustment of first electrode 48A from '1.1' to '1.3'. In an example where field 214B has a prepopulated electrical current value indicating an electrical current amplitude for electrode 48B, the field 214B may display a same value before and after the adjustment to first electrode 48A.

In some examples, a user may adjust electrical current amplitudes and other parameters using user interface 59, but the changes may not go into effect until a user provides an explicit command via user interface 59. For example, a user may adjust electrode 48A from '1.1 mA' to '1.3 mA', but may desire that electrode 48B stay at a current value of '1.2 mA'. In accordance with various techniques of this disclosure, regardless of whether an explicit command is used or not, the user may adjust electrode 48A from '1.1 mA' to '1.3 mA' using field 214B and field 214B may display '1.2 mA' before and after the adjustment, indicating that the electrical current amplitude for electrode 48B remains unchanged from '1.2 mA'. User input received via user interface 59 may be transferred from programmer 40 to electrical stimulator 4. That is electrical stimulator 4 may receive user input from programmer 40 and implement various programming requests accordingly.

Figure 4:
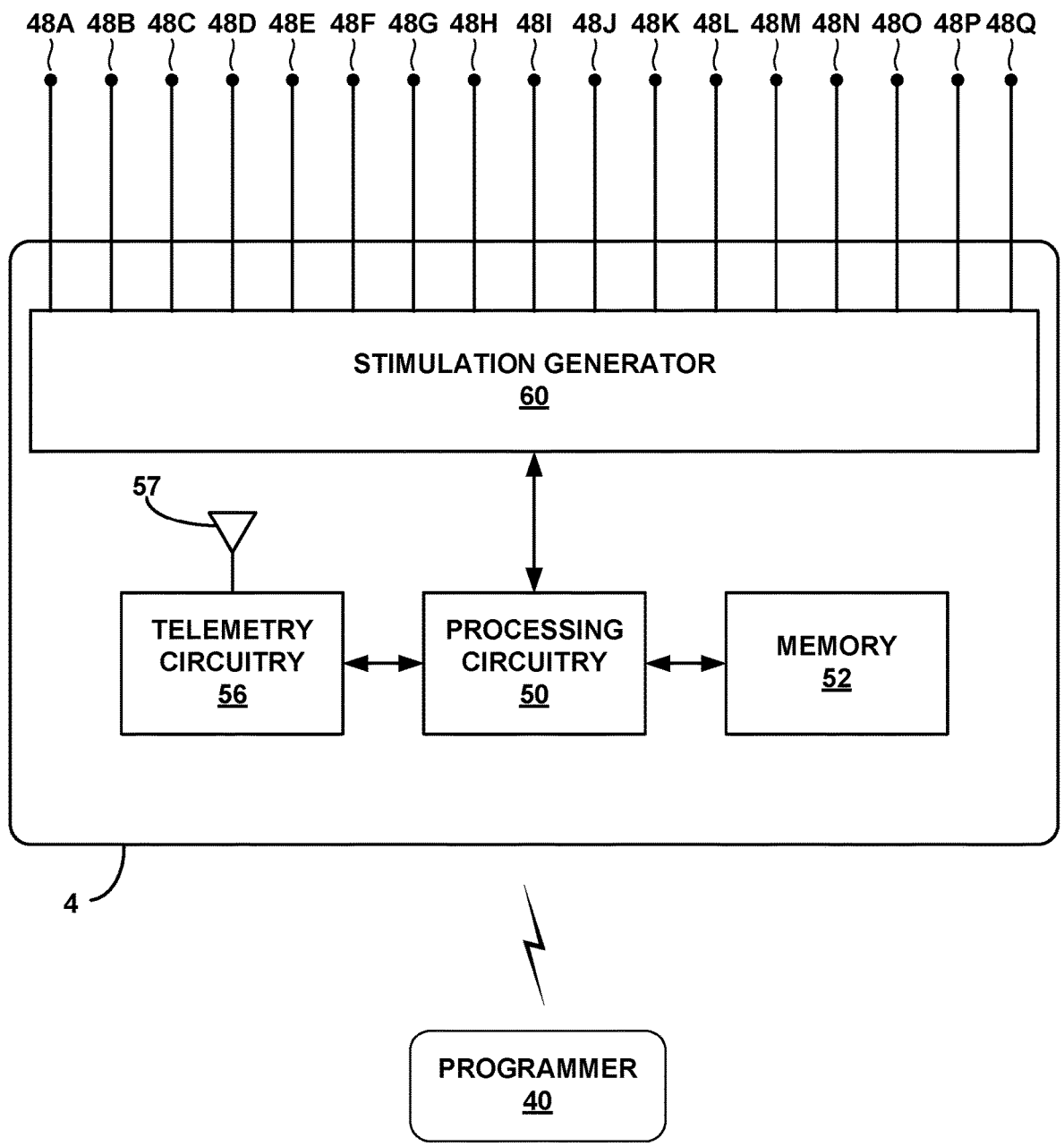
FIG. 4 is a block diagram illustrating various example components of an electrical stimulator, such as the electrical stimulator shown in FIG. 1, in accordance with various techniques of this disclosure.
Figure 5:
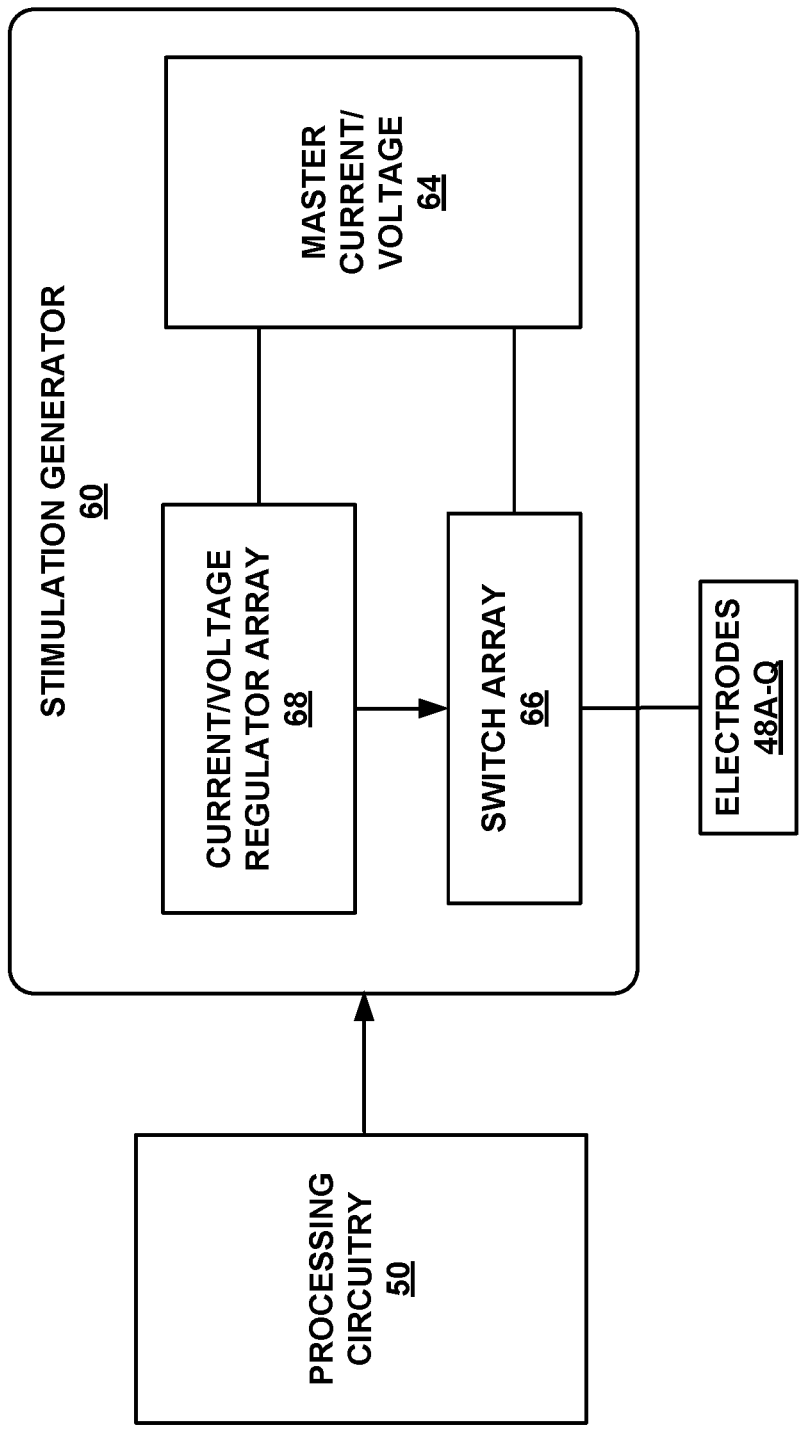
FIG. 5 is a block diagram illustrating various components of an example electrical stimulation generator for use with an electrical stimulator, such as the electrical stimulator of FIGS. 1 and/or 4.

FIG. 4 is a block diagram illustrating various components of an example electrical stimulator 4 that in some examples, may communicate wirelessly with programmer 40 as indicated. In some examples, electrical stimulator 4 includes processing circuitry 50, memory 52, telemetry circuitry 56, antenna 57, and a stimulation generator 60. Stimulation generator 60 is also shown in FIG. 5 coupled to electrodes 48A-Q (collectively "electrodes 48"). In some examples, electrodes 48A-48P may be implantable and may be deployed on one or more leads 12. With respect to FIG. 1, lead segments 12A and 12B may carry electrodes 48A-H and electrodes 48I-P, respectively. In some cases, one or more additional electrodes may be located on or within the housing of electrical stimulator 4, e.g., to provide a common or ground electrode or a housing anode. In some examples, a lead or lead segment carries eight electrodes to provide a 2×8 electrode configuration (two leads with 8 electrodes each), providing a total of sixteen different electrodes.

In some examples, different electrode configurations comprising a single lead, two leads, three leads, or more may be provided. In addition, electrode counts on leads may vary and may be the same or different from a lead to lead. Examples of other configurations include one lead with eight electrodes (1×8), one lead with 12 electrodes (1×12), one lead with 16 electrodes (1×16), two leads with four electrodes each (2×4), three leads with four electrodes each (3×4), three leads with eight electrodes each (3×8), three leads with four, eight, and four electrodes, respectively (4-8-4), two leads with 12 or 16 electrodes (2×12, 2×16), two or more leads with 11 or 13 electrodes, or other configurations. Processing circuitry 50 may select different electrodes to form various electrode combinations. In addition, processing circuitry 50 may assign various polarities to the selected electrodes to designate the electrodes as anodes or cathodes and form additional electrode configurations therefrom.

Electrode 48Q represents one or more electrodes that may be carried on a housing of electrical stimulator 4. Electrode 48Q may also be a dedicated short lead extending from the housing, or a proximal portion of one of the leads carrying electrodes 48A-48P. The proximal portion may be closely adjacent to the housing, e.g., at or near a point at which a lead is coupled to the housing. Electrode 48Q may be configured as a regulated or unregulated electrode for use in an electrode configuration with selected regulated and/or unregulated electrodes among electrodes 48A-48P, which may be located on a lead body of one or more leads, as described above. Electrode 48Q may be formed together on a housing that carries the electrode and houses the components of electrical stimulator 4, such as stimulation generator 60, processing circuitry 50, memory 52, and telemetry circuitry 56.

Housing electrode 48Q may be configured for use as an anode to source current substantially simultaneously with one or more electrodes 48A-48P configured for use as cathodes sinking current in a unipolar arrangement. Housing electrode 48Q may be configured for use as an anode to source current substantially simultaneously with current sourced by another electrode 48A-48P configured for use as an anode in an omnipolar arrangement. By way of specific example, electrodes 48A, 48B, and housing electrode 48Q each could be configured for use as anodes. Electrodes 48A, 48B could deliver electrical stimulation current substantially simultaneously with the electrical stimulation current delivered via housing electrode 48Q. In this illustration, one or more cathodes could be formed with other electrodes (e.g., any of electrodes 48C-48P) on the leads to sink current sourced by anodes 48A, 48B and 48Q.

Memory 52 may store instructions for execution by processing circuitry 50, stimulation therapy data, sensor data, and/or other information regarding therapy for patient 6. Processing circuitry 50 may control stimulation generator 60 to deliver stimulation according to a selected one or more of a plurality of programs or program groups stored in memory 52. Memory 52 may include any electronic data storage media, such as RAM, ROM, EEPROM, NVRAM, flash memory, magnetic memory, or the like. Memory 52 may store program instructions that, when executed by processing circuitry 50, cause the processing circuitry to perform various functions ascribed to processing circuitry 50 and electrical stimulator 4 in this disclosure.

Processing circuitry 50 may include one or more microprocessors, DSPs, ASICs, FPGAs, or other digital logic circuitry. Processing circuitry 50 controls operation of electrical stimulator 4. For example, processing circuitry 50 may control stimulation generator 60 to deliver stimulation therapy according to a selected program or group of programs retrieved from memory 52. In some examples, processing circuitry 50 may control stimulation generator 60 to deliver electrical signals, e.g., as stimulation pulses or continuous waveforms, with current amplitudes, pulse widths (if applicable), and rates specified by one or more stimulation programs. Processing circuitry 50 may also control stimulation generator 60 to selectively deliver stimulation via subsets of electrodes 48, also referred to as electrode combinations, and with polarities specified by one or more programs. The functions attributed to processing circuitry 50 herein may be embodied as software, firmware, hardware or any combination thereof.

Upon selection of a particular program group, processing circuitry 50 may control stimulation generator 60 to deliver stimulation according to programs in the groups. Each program may specify a set of stimulation parameters, such as amplitude, pulse width and pulse rate, if applicable. For a continuous waveform, parameters may include amplitude and frequency. In addition, each program may specify a particular electrode combination for delivery of stimulation, and an electrode configuration in terms of the polarities and regulated/unregulated status of the electrodes. The electrode combination may specify particular electrodes in a single array or multiple arrays, and on a single lead or among multiple leads. The electrode combination may include at least one anode on the housing of the electrical stimulator 4 (e.g., electrode(s) 48Q), at least one anode on a lead, and at least one cathode on a lead. The lead-borne anode and cathode may be on the same lead or different leads, if more than one lead is provided. A program may be defined directly, by selecting parameters and electrodes, or by zone-based programming, in which parameters and electrodes are automatically determined by the programmer in response to manipulation or positioning of stimulation zones.

Stimulation generator 60 is electrically coupled to electrodes 48A-P via conductors of the respective lead, such as lead 12 in FIG. 1. Stimulation generator 60 may be electrically coupled to one or more housing electrodes 48Q via an electrical conductor disposed within the housing of electrical stimulator 4. Housing electrode 48Q may be configured as a regulated or unregulated electrode to form an electrode configuration in conjunction with one or more of electrodes 48A-48P. Housing electrode 48Q may be configured for use as an anode to source current substantially simultaneously with one or more electrodes, e.g., any of electrodes 48A-48P, on one or more leads configured for use as anodes.

Stimulation generator 60 may include stimulation generation circuitry to generate stimulation pulses or waveforms and circuitry for switching stimulation across different electrode combinations, e.g., in response to control by processing circuitry 50. Stimulation generator 60 produces an electrical stimulation signal in accordance with a program based on control signals from processing circuitry 50.

In one example implementation, e.g., an omnipolar arrangement, stimulation generator 60 may be configured to deliver stimulation using one or more of electrodes 48A-P as stimulation electrodes, e.g., anodes, while substantially simultaneously delivering stimulation using housing electrode 48Q as a stimulation electrode, e.g., anode. The anodes on the lead(s) and the housing may be used to deliver stimulation in conjunction with one or more cathodes on the lead(s). As one illustration, an electrode combination selected for delivery of stimulation current may comprise a housing anode, and anode on a lead, and a cathode on the same lead or a different lead. In other examples, the electrode combination may include multiple anodes and/or multiple cathodes on one or more leads in conjunction with at least one anode on housing 14. In some examples, the electrode combination may include one or more anodes on one or more leads, and one or more cathodes on the same lead or a different lead, e.g., a bipolar/multipolar arrangement. In other examples, the electrode combination may include an anode on the housing, and one or more cathodes on one or more leads, e.g., omnipolar arrangement. In yet another example, the electrode combination may include a cathode on the housing, and one or more additional cathodes on one or more leads, along with one or more anodes also on the leads, e.g., a variation of an omnipolar arrangement.

Telemetry circuitry 56 may include a RF transceiver to permit bi-directional communication between electrical stimulator 4 and programmer 40. Telemetry circuitry 56 may include an antenna 57 that may take on a variety of forms. For example, antenna 57 may be formed by a conductive coil or wire embedded in a housing associated with medical device 4. In some examples, antenna 57 may be mounted on a circuit board carrying other components of electrical stimulator 4 or take the form of a circuit trace on the circuit board. In this way, telemetry circuitry 56 may permit communication with programmer 40 in FIG. 1, to receive, for example, new programs or program groups, or adjustments to programs or program groups. Telemetry circuitry 56 may be similar to telemetry circuitry 58 of programmer 40.

FIG. 5 is a block diagram illustrating various components of an example stimulation generator 60. Stimulation generator 60 may be used with an electrical stimulator, e.g., to perform the functions of stimulation generator 60 as described with reference to FIG. 4. In the example of FIG. 4, stimulation generator 60 is selectively configured to deliver current stimulation pulses to patient 6 via electrodes 48. However, this disclosure is not limited to examples in which regulated current pulses are delivered. In other examples, stimulation generator 60 may provide continuous, regulated current waveforms, rather than regulated current pulses. In some examples, stimulation generator 60 may deliver combinations of continuous waveforms and pulses, or selectively deliver either continuous waveforms or pulses. Stimulation generator 60 may generate either constant current-based or constant voltage-based stimulation in the form of pulses or continuous waveforms. Stimulation generator 60 may also be controlled to provide constant power (current-voltage product) or controlled charge stimulation pulses.

In the example illustrated in FIG. 5, stimulation generator 60 includes master current/voltage 64, and current/voltage regulator array 68. In some examples, stimulation generator 60 may further include a switch array 66. Master current/voltage 64 may provide operating power to current/voltage regulator array 68, and may include a regulated current or regulated voltage that sets the level of the master current (e.g., master electrical current amplitude) or master voltage.

As shown in FIG. 5, master current/voltage 64 may be coupled to provide operating power for the current/voltage regulator array 68 and provide a master current, or master voltage when appropriate, for connection to electrodes 48. The maximum operating current level and the master current level provided to regulate current regulator array 68 may be different at any given time. For example, a master electrical current amplitude may be less than the maximum operating current level, such that the master electrical current amplitude may be increased or decreased according to minimum and maximum operating conditions. In some examples, as described with reference to FIG. 3, user interface 59 may display such information for a user to reference while adjusting electrical current amplitudes for various electrodes.

Processing circuitry 50 may control (e.g., via a stimulation controller) switch array 66 and current/voltage regulator array 68 to deliver stimulation via electrodes 48. In operation, processing circuitry 50 may control delivery of electrical stimulation according to one or more programs that may specify stimulation parameters such as electrode combination, electrode polarity, stimulation current amplitude, pulse rate, and/or pulse width as well as the percentage of source current distributed among or contributed by a housing anode and one or more lead anodes on one or more leads, and the percentage of sink current sunk by one or more cathodes. Programs may be defined by a user via an external controller and downloaded to an electrical stimulator 4.

Current/voltage regulator array 68 includes a plurality of regulated current sources or sinks. A current regulator may function as either a current source or sink, or be selectively configured to operate as either a source or a sink. In some examples, current/voltage regulator array 68 may regulate voltage instead of, or in addition to, current. For convenience, the term "current regulator" may be used in some instances to refer to either a source or sink. Hence, each of the current regulators in current/voltage regulator array 68 may operate as a regulated current source that delivers stimulation via a corresponding one of electrodes 48 or a regulated current sink that receives current from a corresponding one of electrodes 48, where electrodes 48 may be provided on leads, on a stimulator housing, on a leadless stimulator, or in other arrangements.

Each current regulator may correspond to a plurality of current regulator branches. In some examples, the current regulator branches may be implemented in a parallel, such as with parallel current regulator branches. The number of current regulator branches defines the resolution for each current regulator. For example, the number of current regulator branches may be 64 in some examples, such that the electrical current amplitude may be adjusted for a given electrode in 1/64 increments (i.e., a resolution of 1/64). While 64 current branches are used for example throughout this disclosure, the techniques of this disclosure are not so limited, and the number of current branches may be more or fewer than 64 branches. For example, in some implementations, 128 current branches may be used, such that the current regulator for a particular electrode may be adjusted in 1/128 increments (i.e., a resolution of 1/128). In an illustrative example implementation with a resolution of 1/64, a ring electrode at full output may implement 64 branches (e.g., $64/64^{ths}$). In addition, stimulation generator 60 may be set such that, for each of the highest contributing electrodes of the highest intensity active zone, all 64 parallel current regulator branches are used.

In examples involving segmented leads (e.g., segmented electrodes), electrodes at various axial positions of lead 12 may have a fraction maximum equal to approximately the number of branches available to the electrode divided by the number of electrodes segments in a ring of segmented electrodes. For example, ring electrodes may have a maximum of 64/64 fractions in an example involving 64 current regulator branches, whereas each of N segmented electrodes in a ring of segmented electrodes may have a maximum of approximately 64/N fractions. In an illustrative example, in the case of three segmented electrodes in a ring, each electrode may have a fraction maximum of 21/64 fractions. In some examples, the fraction maximum for any given electrode, including ring electrodes, may reach the full number of current regulator branches (e.g., 64 branches). That is, processing circuitry 53 or processing circuitry 50 may be configured to impose any fraction maximum based on the particular stimulation generator 60 in use (e.g., the number of current regulator branches). For example, in the case of three segmented electrodes in a ring as in the previous example, each electrode may have a fraction maximum of X/X fractions (e.g., 64/64 fractions) or a fraction less than X/X that has been predefined by processing circuitry 53 or processing circuitry 50.

In examples including switch array 66, each switch of switch array 66 may couple a corresponding one of electrodes 48 to either a corresponding bi-directional current regulator of current/voltage regulator array 68 or to master current/voltage 64. In some examples, processing circuitry 50 selectively opens and closes switches in switch array 66 to configure a housing electrode (e.g., electrode(s) 48Q), and one or more of electrodes 48A-48P on one or more leads as regulated electrodes by connection to regulated current sources or sinks in current/voltage regulator array 68. In some examples, processing circuitry 50 may selectively open and close switches in switch array 66 to configure either the housing electrode, e.g., electrode 48Q, or an electrode on the lead as an unregulated electrode by connection to master current/voltage 64. In addition, processing circuitry 50 may selectively control individual regulated current sources or sinks in current/voltage regulator array 68 to deliver stimulation current pulses to the selected electrodes. In examples where switch array 66 is not used, electrodes 48 may nevertheless be coupled to current/voltage regulator array 68 and/or to master current/voltage 64.

Master current/voltage 64 may be a high or low voltage supplied by a regulated power source, depending on whether an electrode is programmed to be an unregulated source (high voltage rail) or unregulated sink (low voltage rail). Hence, master current/voltage 64 may produce high and low master current, or master voltages when appropriate, for selective coupling to unregulated, reference electrodes as needed. A regulated power source may produce one or more regulated voltage levels for use as master current/voltage 64 and for use as a power rail for current/voltage regulator array 68. Although the same master current/voltage 64 is shown as being coupled to current/voltage regulator array 68 in FIG. 5, different current amplitude may be used for the master current coupled to switch array 66 and the maximum current amplitude provided to current regulator array 68. In any event, a regulated power source may generate the regulated current amplitudes from current provided by a power source or multiple power sources, such as one or more batteries (e.g., rechargeable batteries).

Processing circuitry 50 controls the operation of switch array 66 to produce electrode configurations defined by different stimulation programs. In some cases, the switches of switch array 66 may be metal-oxide-semiconductor field-effect-transistors (MOSFETs) or other circuit components used for switching electronic signals. The switches of switch array 66 may be designed to carry an amount of unregulated current that may be coupled to a corresponding electrode through an unregulated current path associated with master current/voltage 64. In some examples, two or more regulated electrodes 48 may be intentionally programmed to deliver different amounts of current, such that the regulated electrodes produce an unbalanced current distribution. In other examples, regulated source and sink current may be balanced such that substantially all current may be sourced and sunk via respective regulated current sources and sinks.

To provide individual control of electrodes 48 as either regulated electrodes or as unregulated, reference electrodes, processing circuitry 50 controls operation of switch array 66 and current/voltage regulator array 68. When stimulation is delivered to patient 6, for the example of current pulses, processing circuitry 50 controls switch array 66 to couple selected stimulation electrodes for a desired electrode combination to respective current regulators of current/voltage regulator array 68 or to master current/voltage 64, as needed. Processing circuitry 50 controls the regulated bi-directional current sources of current/voltage regulator array 68 coupled to regulated electrodes to source or sink specified amounts of current. For example, processing circuitry 50 may control selected current sources or sinks on a pulse-by-pulse basis to deliver current pulses to corresponding electrodes.

Processing circuitry 50 also deactivates the regulated bi-directional current regulators of current/voltage regulator array 68 tied to inactive electrodes, e.g., electrodes that are not active as regulated electrodes in a given electrode configuration. Each regulated bidirectional current regulator of current/voltage regulator array 68 may include an internal enable switch controlled by processing circuitry 50 that disconnects regulated power from the current regulator or otherwise disables the current source when the corresponding electrode is not used as a regulated electrode.

Figure 6:
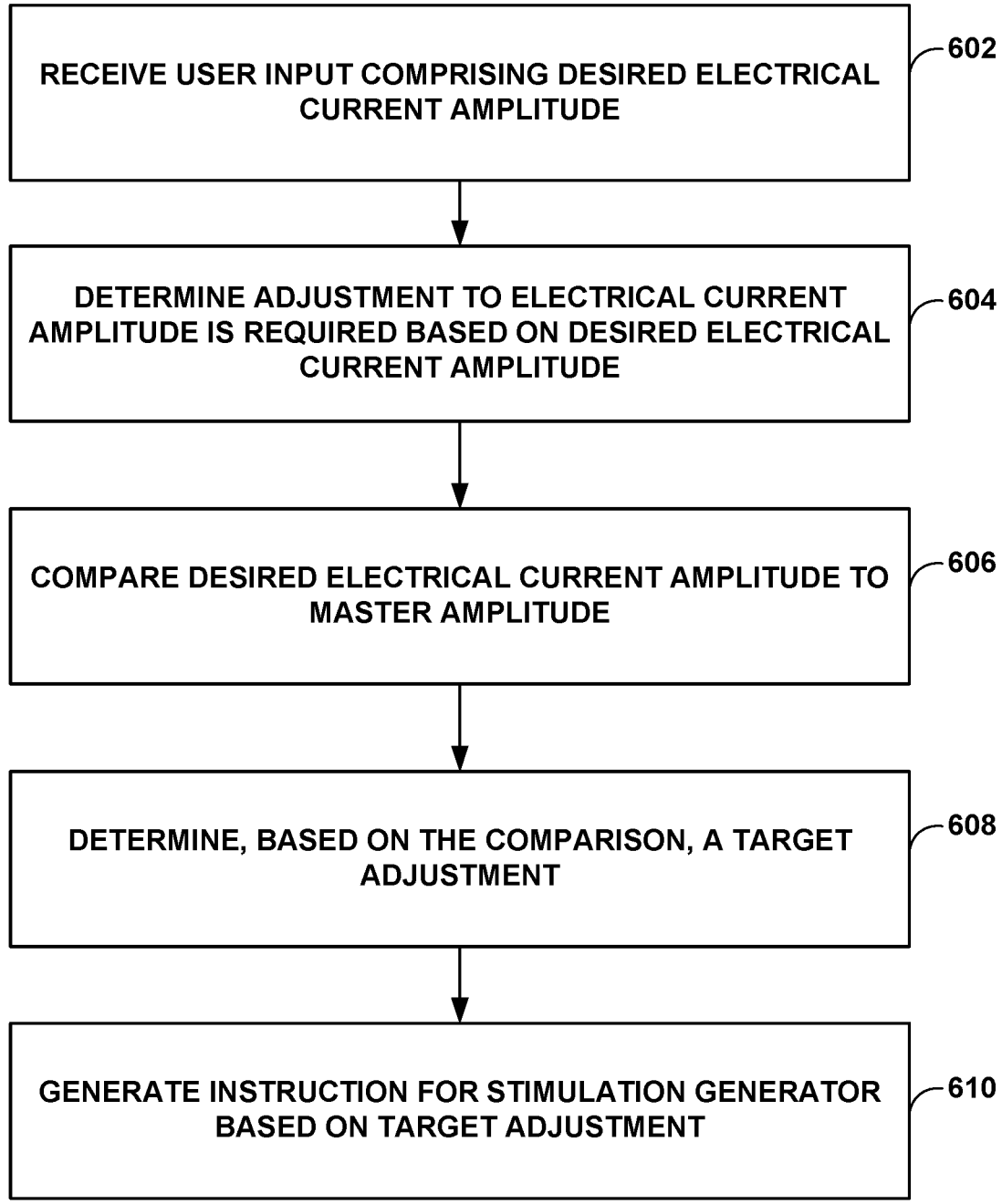
FIGS. 6-9 are flowcharts illustrating example methods for performing the techniques of this disclosure.

FIG. 6 is a flowchart illustrating an example method for controlling a neuromodulation system, such as system 2 of FIG. 1, in accordance with various techniques of this disclosure. The neuromodulation system may include at least two electrodes 48 and stimulation generator 60. Stimulation generator 60 may be configured to deliver first stimulation pulses to a first electrode 48A of the at least two electrodes 48, and second stimulation pulses to a second electrode 48B. In such examples, stimulation generator 60 may deliver first stimulation pulses to first electrode 48A at a first electrical current amplitude and may deliver second stimulation pulses to second electrode 48A at a second electrical current amplitude. The first electrical current amplitude may be implemented using a first fraction of a master amplitude and the second electrical current amplitude of the second stimulation pulses may be implemented using a second fraction of the master amplitude, as discussed above with reference to FIG. 5. In some examples, the neuromodulation system may include a third electrode to provide a return path for at least a portion of the stimulation pulses.

Although described as being performed by electrical stimulator 4, the example method of FIGS. 6-9 may be performed by any one or more of programmer 40, electrical stimulator 4, an external device or server (e.g., a remote server), or a combination of one or more of these devices, e.g., by the processing circuitry of any one or more of these devices. In one example, processing circuitry 53 may determine adjustments to fractions and amplitudes based on user input via user interface 59. Programmer 40 may then transmit the determined adjustments to electrical stimulator 4, where electrical stimulator 4 may implement the adjustments. In another example, processing circuitry 53 may receive the user input and transmit the user input to the electrical stimulator 4, where electrical stimulator 4 may determine adjustments to electrical stimulator 4 in accordance with various techniques of this disclosure.

In some examples, electrical stimulator 4 may transmit information to programmer 40 for display, such as adjusted master amplitude values, electrical current amplitude values of stimulation pulse, and/or fractional values. Programmer 40 may store to memory 55 such information and in some examples, use the information to determine further adjustments for electrical stimulator 4. Similarly, electrical stimulator 4 may store adjustment requests received, from programmer 40, to memory 52 for subsequent implementation. In some examples, electrical stimulator 4 may perform the methods of one or more of FIGS. 6-9 based on input received from another device, such as a remote server or programmer 40. Electrical stimulator 4 may then adjust various parameters in accordance with various techniques of this disclosure, and communicate the adjustments or a partial summary of the adjustments, such as only electrical current values, to programmer 40 or another user interface device for display.

Processing circuitry 50 for an electrical stimulator 4 may receive user input comprising a desired electrical current amplitude (602). For example, processing circuitry 50 may receive the desired electrical current amplitude from processing circuitry 53 of programmer 40. Processing circuitry 53 may transfer the desired electrical current amplitude as provided by a user via fields 214A or 214B of user interface 59 to processing circuitry 50. In some examples, processing circuitry 50 may first generate instructions for stimulation generator 60 to deliver the first simulation pulses based on a first fraction of a master amplitude, and deliver the second stimulation pulses based on a second fraction of the master amplitude, such as where stimulation pulses are already implemented at particular amplitudes and the user desired to adjust the amplitudes. In some examples, the user may program the amplitudes anew in which case the initial instruction may be to deliver at a zero amplitude until a user sets a desired current amplitude.

Responsive to the user input, processing circuitry 50 may determine that the user input indicates an adjustment to the first electrical current amplitude of the first stimulation pulses is required (604). For example, the original first electrical current amplitude prior to adjustment may be 0 mA or may be a non-zero value, such as 1.1 mA. The user input may be a value greater than the original value, such as 1.2 mA or in some instances, may be less than the original value 0.9 mA indicating a requested decrease in electrical current amplitude. In any event, processing circuitry 50 may determine that the user input indicates a requested adjustment to the first electrical current amplitude of the first stimulation pulses from the original value to an adjusted value that is either greater than or less than the original value.

Based on the user input comprising a desired electrical current amplitude, processing circuitry 50 may compare the desired electrical current amplitude to the master amplitude or otherwise determine whether the desired electrical current amplitude is equal to, less than, or greater than the master amplitude (606). For example, processing circuitry 50 may receive an indication as to whether the desired electrical current amplitude is greater than, equal to, or less than the master electrical current amplitude from another device. In some examples, processing circuitry 53 may convey comparison information to processing circuitry 50 indicating that the desired electrical current amplitude is equal to, less than, or greater than the master amplitude.

Processing circuitry 50 may determine a target adjustment based at least in part on a comparison of the desired electrical current amplitude to the master amplitude (608). For example, processing circuitry 50 may utilize a first fraction adjustment scheme as the target adjustment that adjusts the first fraction of electrode 48A. Processing circuitry 50 may utilize a second fraction adjustment scheme as the target adjustment that adjusts the second fraction of electrode 48B and an adjustment to the master amplitude. The first and second fraction adjustments are illustrated further with reference to FIG. 7.

Based on the particular fraction adjustment selected as the target adjustment, processing circuitry 50 may generate an instruction (e.g., an adjustment instruction) for stimulation generator 60 to deliver the first stimulation pulses at the desired electrical current amplitude and deliver the second stimulation pulses at approximately the same second electrical current amplitude that was being delivered to the second electrode prior to the adjustment to the first fraction (610). That is, processing circuitry 50 may utilize the target adjustment to adjust the first current amplitude to achieve the desired electrical current amplitude, while maintaining the second stimulation pulses at the same or approximately the same amplitude. The approximation may be due to the finite resolution available with the particular number of current regulator branches. For example, the second fraction adjustment may result in an increase of the master amplitude and a decrease of the second fraction relative to the master amplitude increase, such that the second amplitude maintains as close to the original second amplitude as possible.

As mentioned, the exact same amplitude may not be possible, but due to particular rounding rules, the display on user interface 59 may display the same current amplitude. In an illustrative example involving a 64 branch regulator, the second current amplitude may be 1.1 mA and the adjusted master amplitude may be 2 mA. As such, processing circuitry 50 may program the second fraction to be 35/64, which actually equals 1.09 mA, but 35/64 the fraction that will maintain the second electrical current amplitude as close to 1.1 mA as possible. However, user interface 59 may round 1.09 mA up to 1.1 mA when displaying the current values, and thus, to a user, the second electrical current may remain the same, despite having an adjustment to the second fraction and the master amplitude.

In some examples, electrical stimulator 4 continues to deliver electrical stimulation to patient 6 during the transition from a first electrical current amplitude to a subsequent electrical current amplitude, thus preventing the need to ramp the intensity up after the transition. Although in some examples, the user may be limited to adjusting the electrical current amplitude for one electrode at a given time, some examples may allow the user to adjust the electrical current amplitude for multiple electrodes simultaneously. For example, a user may be able to input desired electrical current amplitudes for multiple electrodes at one time, and as such, processing circuitry 50 may select a particular fraction adjustment in accordance with various techniques of this disclosure.

In examples involving processing circuitry 53 determining the fraction and master amplitude adjustments based on user input, processing circuitry 53 may be configured to provide the adjustment instruction to processing circuitry 50 via telemetry circuitry 53. Likewise, processing circuitry 50 may be configured to receive the adjustment instruction from processing circuitry 53 via telemetry circuitry 58. In any event, the adjustment instruction output to electrical stimulator 4 (e.g., stimulation generator 60) may include fractional values, amplitude values, or a combination thereof. For example, programmer 40 may output an adjustment instruction to electrical stimulator 4 instructing stimulation generator 60 to adjust the fractional value for any one of electrodes 48 from a first fraction to an adjusted fraction in order to achieve a desired electrical current amplitude defined by the user input.

Figure 7:
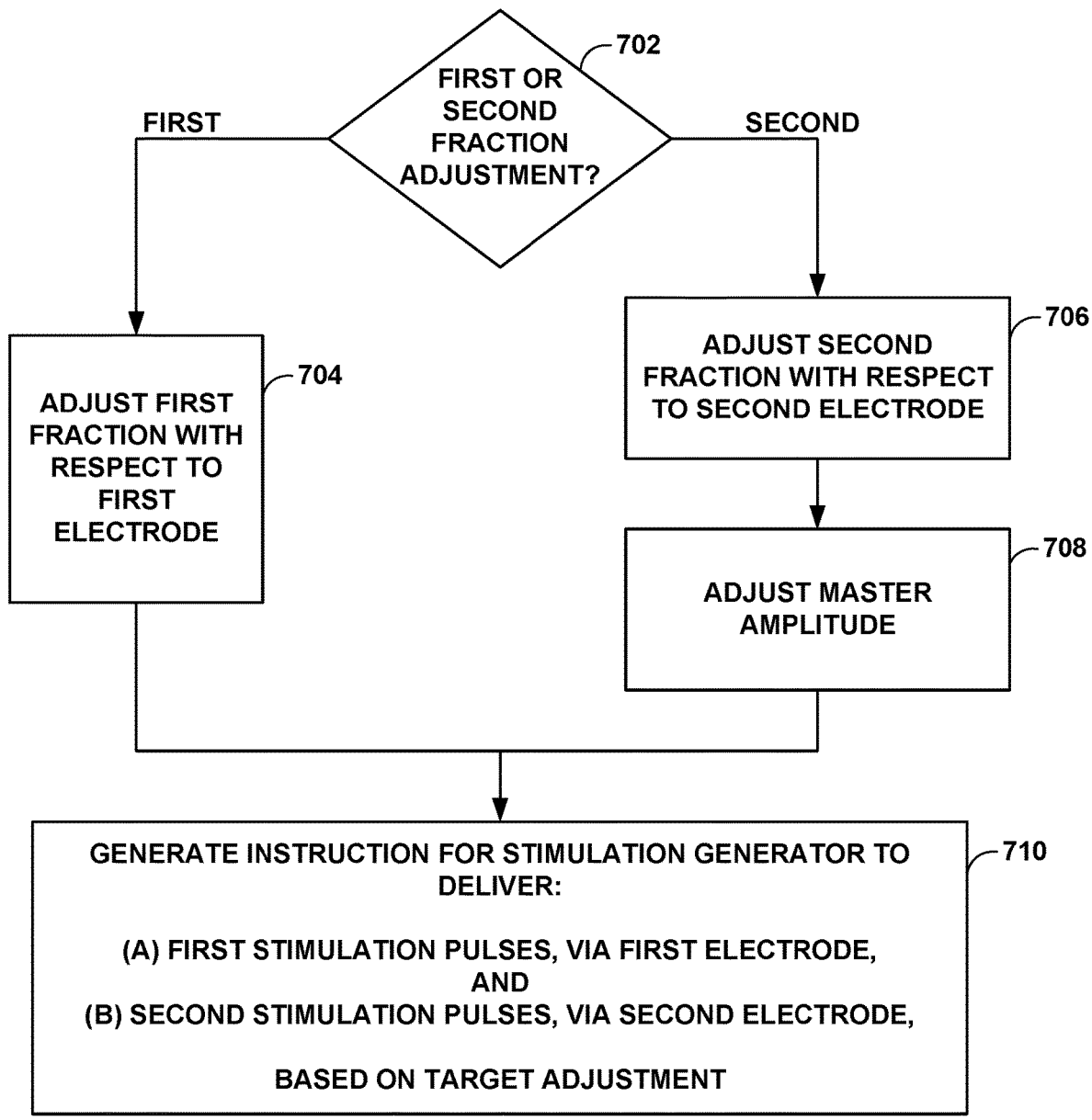

FIG. 7 is a flowchart illustrating a difference between first and second fraction adjustments implemented with respect to the method of FIG. 6. As stated above, although described as being performed by electrical stimulator 4, the example method of FIG. 7 may be performed by any one or more of electrical stimulator 4, programmer 40, an external device or server (e.g., a remote server), or a combination of one or more of these devices, e.g., by the processing circuitry of any one or more of these devices.

In an example involving an adjustment to the electrical current amplitude for first electrode 48A, processing circuitry 50 may determine whether to implement a first or second fraction adjustment scheme (702). As described above, processing circuitry 50 may utilize one of the first or second fraction adjustments based at least in part on a comparison of the desired electrical current amplitude for the first electrode and the master electrical current amplitude.

When the first fraction adjustment is utilized, processing circuitry 50 may adjust the first fraction with respect to electrode 48A (704). It should be noted that when the first fraction adjustment is utilized as the target adjustment, the first fraction is adjusted, and the second fraction may be adjusted, as well.

When the second fraction adjustment is utilized, processing circuitry 50 may adjust the second fraction with respect to electrode 48B (706). In addition, processing circuitry 50 may adjust the master amplitude (708). It should be noted that when the second fraction adjustment is utilized as the target adjustment, the second fraction is adjusted, the master amplitude is adjusted, and the first fraction may be adjusted, as well. In some instances, however, the first fraction may not be adjusted depending on the desired change in electrical current amplitude, the current electrode configuration, and/or the current master amplitude. Processing circuitry 50 may generate an instruction (e.g., an adjustment instruction) for stimulation generator 60 to deliver the first stimulation pulses, via first electrode 48A, and deliver the second stimulation pulses, via second electrode 48B, based on the target adjustment (710).

While a first fraction adjustment scheme and a second fraction adjustment scheme are described as being potential target adjustments, the techniques of this disclosure are not so limited. In some examples, processing circuitry 50 may perform a combination of the first fraction adjustment scheme and second fraction adjustment scheme. For example, processing circuitry 50 may transition between the first fraction adjustment and the second fraction adjustment to achieve the desired electrical current amplitude. In one example, processing circuitry 50 may perform the first fraction adjustment to adjust a fraction for first electrode 48A. Processing circuitry 50 may determine that the adjustment to the fraction for first electrode 48A results in a trigger for the master amplitude to be adjusted along with the master amplitude. For example, the first electrode 48A may be the electrode driving the master amplitude because first electrode 48A is delivering the highest amplitude out of the other electrodes and thus, the master amplitude may follow or be driven by the highest amplitude delivered to an electrode. The adjustment to the fraction for first electrode 48A, however, may include decreasing the fraction for first electrode 48A to achieve a desired electrical current amplitude that is less than the master amplitude. In addition, the decrease in amplitude for the first electrode 48A may be less than the amplitude of second electrode 48B. In such instances, the other electrode may become the driving electrode and the master amplitude may not decrease below the electrical current amplitude defined for second electrode 48B. As such, a combination of the first fraction adjustment scheme and the second fraction adjustment scheme may be required to adjust the master amplitude, the first fraction for first electrode 48A, and the second fraction for second electrode 48A, in succession or as an iterative process. For example, processing circuitry 50 may perform an iterative process between each of the first fraction adjustment scheme and the second fraction adjustment scheme until the desired electrical current amplitude is achieved for all stimulation pulses.

It should be noted that the master amplitude in some instances may be adjusted prior to, in succession with, or following the adjustment to the second fraction. For example, where the target adjustment indicates that the master amplitude is to be adjusted upward (e.g., an increase in master amplitude), the fractional values may be changed first followed by the adjustment to the master amplitude. In another example, where the target adjustment indicates that the master amplitude is to be adjusted downward (e.g., a decrease in master amplitude), the master amplitude may be adjusted first followed by the adjustment to the fractional values. It should also be noted that while electrodes 48A and 48B are used to illustrate various electrodes in various examples of this disclosure, the techniques of this disclosure are not so limited, and any electrode of a lead may be used as a first electrode or second electrode in keeping with the spirit of this disclosure.

Figure 8:
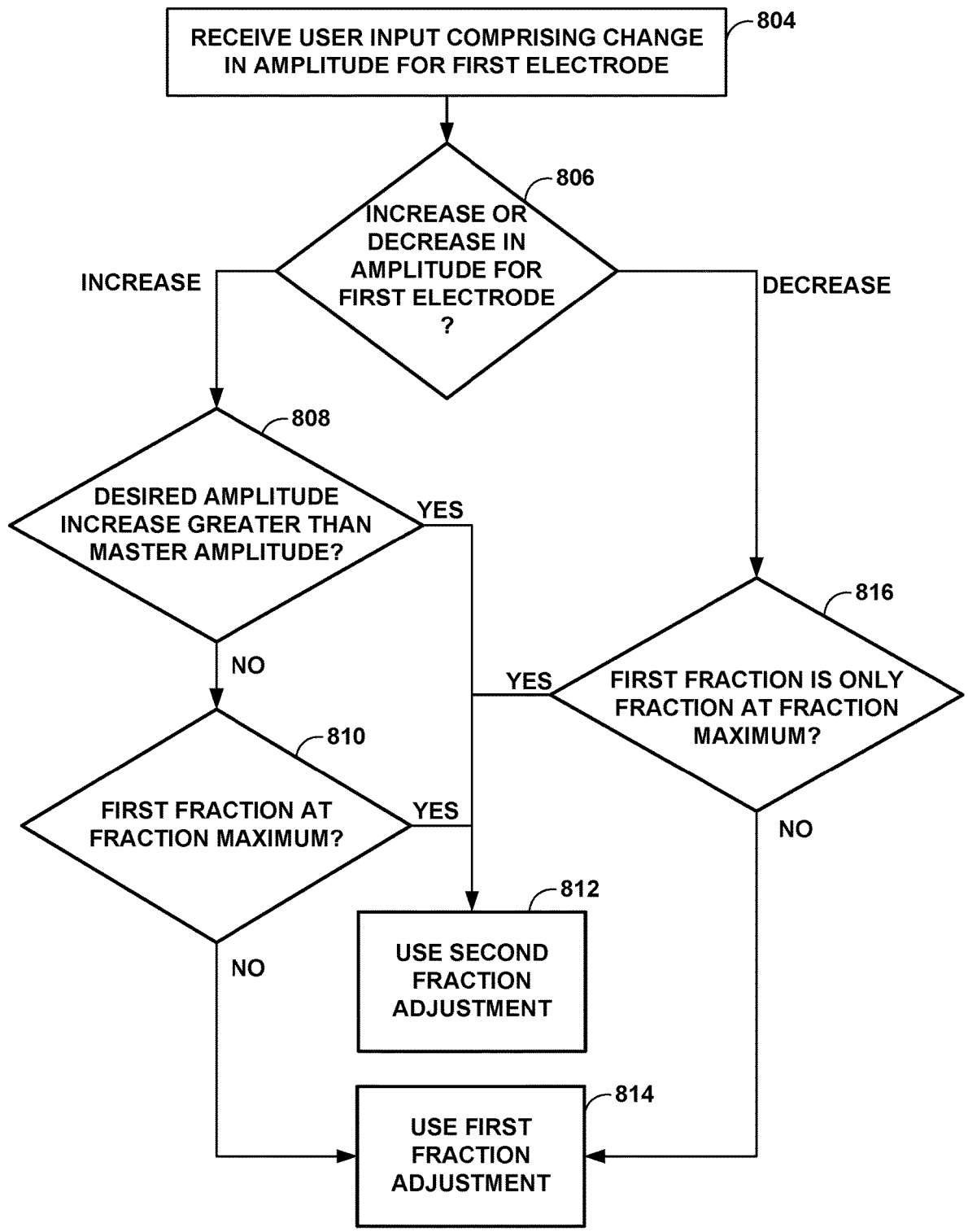

FIG. 8 is a flowchart illustrating an example method for adjusting the first electrical current amplitude for first electrode 48A, while maintaining the electrical current amplitude of second electrode 48B, both of which have amplitudes defined by respective fractions of an adjustable master electrical current amplitude. As stated above, although described as being performed by electrical stimulator 4, the example method of FIG. 8 may be performed by any one or more of electrical stimulator 4, programmer 40, an external device or server (e.g., a remote server), or a combination of one or more of these devices, e.g., by the processing circuitry of any one or more of these devices.

Processing circuitry 50 may receive user input comprising a change in amplitude for first electrode 48A (804). In a non-limiting example, a user may provide user input requesting a change in amplitude for first electrode 48A to increase electrical stimulation delivery from 1.0 mA to 1.1 mA or to decrease electrical stimulation from 1.0 mA to 0.9 mA. As such, processing circuitry 50 may determine whether the adjustment to the amplitude for first electrode 48A comprises an increase or decrease in amplitude for first electrode 48A (806). If the user input indicates a request to increase the first electrical current amplitude, processing circuitry 50 may determine whether the desired electrical current amplitude for first electrode 48A comprises an increase that is greater than the master electrical current amplitude (808). If the desired electrical current amplitude is greater than the master amplitude, then processing circuitry 50 may achieve the desired electrical current amplitude using the second fraction adjustment (812).

For example, if the master amplitude is 1.0 mA and the user input includes a desired electrical current amplitude from 1.0 mA to 1.1 mA, the master amplitude may be increased to 1.1 mA to achieve the desired electrical current amplitude of the first electrode 48A, such that the first fraction of first electrode 48A may remain unchanged. However, because the master amplitude is increased, in order to maintain the second electrical current amplitude at the same value or approximately the same value prior to the user input, the second fraction may be adjusted relative to the adjustment to the master amplitude. For example, the second electrical current amplitude for second electrode 48B may have been 0.5 mA prior to processing circuitry 50 receiving the user input requesting an increase to the first electrical current amplitude for first electrode 48A.

As such, in an example including 64 current regulator branches, the second fraction may have been 32/64 prior to the change in order to achieve 0.5 mA for second electrode 48B with a master amplitude of 1.0 mA (i.e., 1.0 mA*(32/64)=0.5 mA). With the master amplitude increasing from 1.0 mA to 1.1 mA on account of the user input, the second fraction in this example, may be decreased to achieve as close to 0.5 mA as possible based on a fraction of the 1.1 mA master amplitude. Specifically, the second fraction may be decreased to 29/64 or 29 current regulator branches out of 64 total current regulator branches, for a total of approximately 0.498 mA. Due to particular rounding rules that processing circuitry 50 may employ, 0.498 mA may round to 0.5 mA on user interface 59, and thus, to a user, the second amplitude will appear to be unaffected as intended following the user requesting a change to the first amplitude. That is, the second amplitude following adjustment to the second fraction may be approximately the same as the original second amplitude. In examples where the second fraction and the master amplitude remain unchanged, the second amplitude may too remain the same. In any event, the second amplitudes may be the same or approximately the same, meaning within a range that is dependent on the resolution available from the stimulation generator or in other words, the total number of current regulator branches available. This is because a single branch of the total number of branches may be implemented in full so as to increase or decrease a fraction according to a finite step size (e.g., 1/64), and as such, an approximation may be used to achieve an adjusted amplitude as close to the original amplitude as possible as a function of the master amplitude.

If the desired electrical current amplitude is less than the master amplitude, processing circuitry 50 may determine whether the first fraction of first electrode 48A is at a fraction maximum or is at least greater than the second fraction of second electrode 48B (810). If so, processing circuitry 50 may use the second fraction adjustment (812). Otherwise, processing circuitry 50 may use the first fraction adjustment (814). For example, processing circuitry 50 may use the first fraction adjustment to increase the first fraction. In the event of the second fraction adjustment being used, processing circuitry 50 may use the second fraction adjustment to both increase the master amplitude and decrease the second fraction of electrode 48B, in order to achieve the desired electrical current amplitude for the first stimulation pulses of first electrode 48A.

If the user input indicates a request to decrease the first electrical current amplitude, then processing circuitry 50 may automatically determine that the desired decrease in the first electrical current amplitude would result in an amplitude that is less than the master current amplitude if the master current amplitude were not to be decreased accordingly (806). Either way, processing circuitry 50 may determine whether the first fraction is the only fraction at a fraction maximum or is at least greater than the second fraction of second electrode 48B (816). In some instances, determining whether the first fraction is the only fraction at a fraction maximum, processing circuitry 50 may determine that the first fraction for first electrode 48A is at a fraction maximum defined for first electrode 48A, and that the second fraction for second electrode 48B is not at a fraction maximum defined for second electrode 48B. If so, processing circuitry 50 may use the second fraction adjustment scheme as the target adjustment (812). Otherwise, processing circuitry 50 may use the first fraction adjustment (814). For example, processing circuitry 50 may use the first fraction adjustment to decrease the first fraction. In the event of the second fraction adjustment being used, processing circuitry 50 may use the second fraction adjustment to both decrease the master amplitude and increase the second fraction of electrode 48B, in order to achieve the desired electrical current amplitude for the first stimulation pulses of first electrode 48A.

Figure 9:
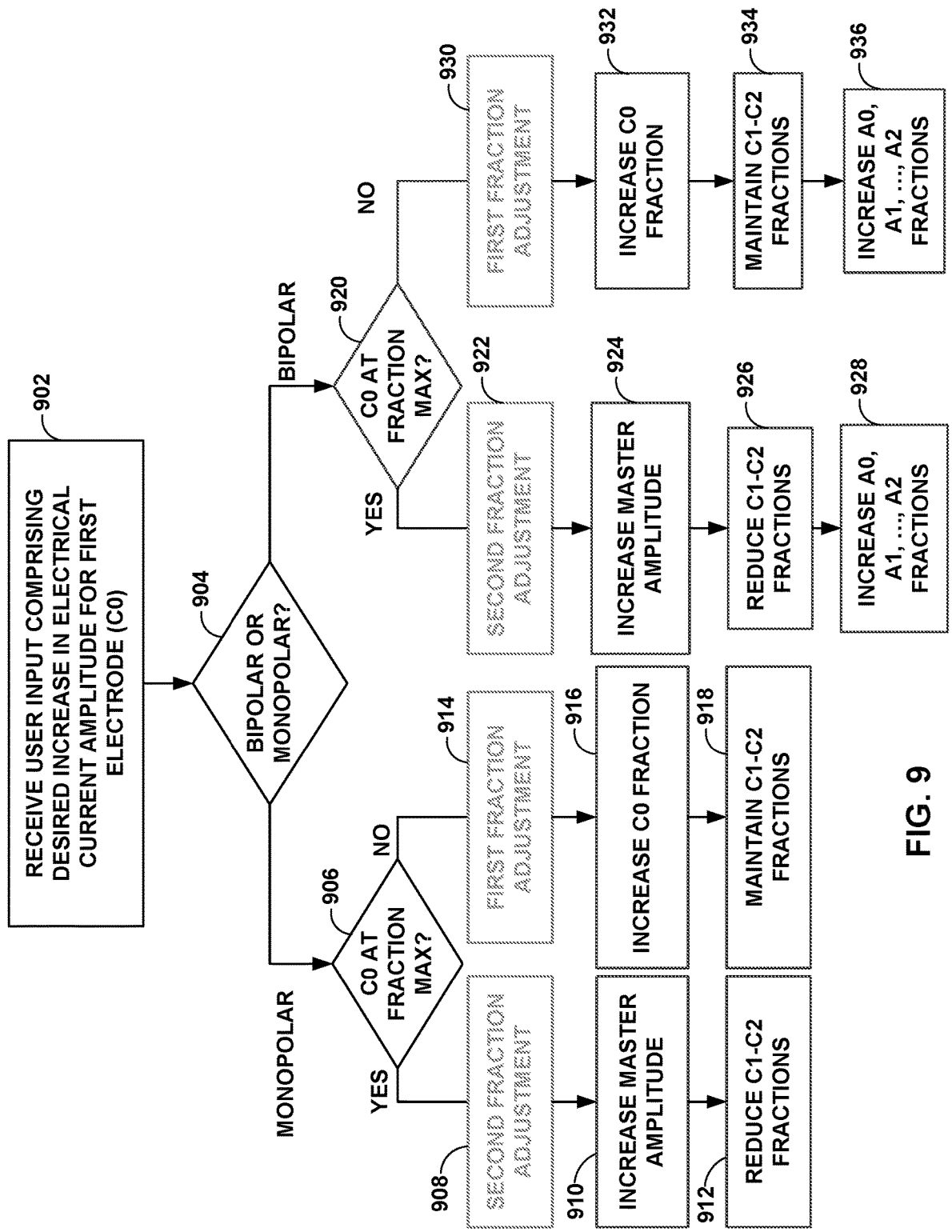

FIG. 9 is a flowchart illustrating an example method for performing the techniques of this disclosure with respect to bipolar and monopolar arrangements. As stated above, although described as being performed by electrical stimulator 4, the example method of FIG. 9 may be performed by any one or more of electrical stimulator 4, programmer 40, an external device or server (e.g., a remote server), or a combination of one or more of these devices, e.g., by the processing circuitry of any one or more of these devices.

At the outset, processing circuitry 50 may receive user input comprising a desired increase in electrical current amplitude for a first electrode (902). For simplicity of illustration, the first electrode may be signified by 'C0' in FIG. 9 to indicate a cathode electrode. In this example, at least three cathode electrodes are described (e.g., C0-C2). However, the number of electrodes may be more or less than three, with three being chosen for illustrative purposes. Other electrodes including an 'A' suffixed may indicate an anode electrode. Processing circuitry 50 may in a first instance, determine whether the electrode configuration supports a bipolar arrangements having at least one regulated anode or whether the electrode configuration supports a bipolar arrangements having at least one unregulated anode (904). Processing circuitry 50 may receive information regarding the particular arrangement at a time prior to the adjustment of current amplitudes. For example, processing circuitry 50 may store to memory 52 at an initial configuration stage what type of electrode arrangement is in use.

A unipolar stimulation arrangement (e.g., monopolar) generally refers to the use of an anode on the housing that sources current and one or more cathodes on one or more leads that sink current. A bipolar stimulation arrangement generally refers to the use of an anode on a lead that sources current and a cathode on the same lead and/or another lead that sink current. A multipolar stimulation arrangement generally refers to the use of one or more anodes (or cathodes) on a lead that each source (or sink) current and one or more cathodes (or anodes) on the same lead or another lead that sink (or source) current, or the use of one anode on a lead that sources current and multiple cathodes on the same lead or another lead that sink current. A hybrid stimulation arrangement that combines both unipolar and bipolar electrode relationships may be referred to as an omnipolar arrangement. Techniques of this disclosure may be implemented using unipolar arrangements, bipolar/multipolar arrangements, and omnipolar arrangements.

In an illustrative example, a bipolar stimulation arrangement may include at least three electrodes, where a third electrode provides a return path for the other two electrodes. In a monopolar stimulation arrangement, a third electrode may be included, but the third electrode may not be used to provide any return path in such monopolar configurations.

In the monopolar configuration, processing circuitry 50 may determine whether C0 is at a fraction maximum or is at least greater than the second fraction of any of second electrodes C1-C2 (920). If so, processing circuitry 50 may use the second fraction adjustment (908). In the event of the second fraction adjustment being used, processing circuitry 50 may use the second fraction adjustment to increase the master amplitude (910). Processing circuitry 50 may also reduce or decrease the second fraction of electrodes C1-C2, in order to achieve the desired electrical current amplitude for the first stimulation pulses of first electrode C1. If C0 is not at a fraction maximum, processing circuitry 50 may use the first fraction adjustment (914). For example, processing circuitry 50 may use the first fraction adjustment to increase the first fraction of C0 (916). In addition, processing circuitry 50 may maintain the C1-C2 fractions at original values prior to the requested adjustment of the electrical current amplitude for the first stimulation pulses of first electrode C1.

In the bipolar configuration, processing circuitry 50 may determine whether C0 is at a fraction maximum or is at least greater than the second fraction of any of second electrodes C1-C2 (920). If so, processing circuitry 50 may use the second fraction adjustment (922). In the event of the second fraction adjustment being used, processing circuitry 50 may use the second fraction adjustment to increase the master amplitude (924). Processing circuitry 50 may also reduce the second fraction of electrodes C1-C2. In addition, processing circuitry 50 may increase fractions associated with electrodes A0-A2. If C0 is not at a fraction maximum, processing circuitry 50 may use the first fraction adjustment (914). For example, processing circuitry 50 may use the first fraction adjustment to increase the first fraction of C0 (916). In addition, processing circuitry 50 may maintain the C1-C2 fractions at original values prior to the requested adjustment of the electrical current amplitude for the first stimulation pulses of first electrode C1. In addition, processing circuitry 50 may increase fractions associated with electrodes A0-A2.

Figure 10:
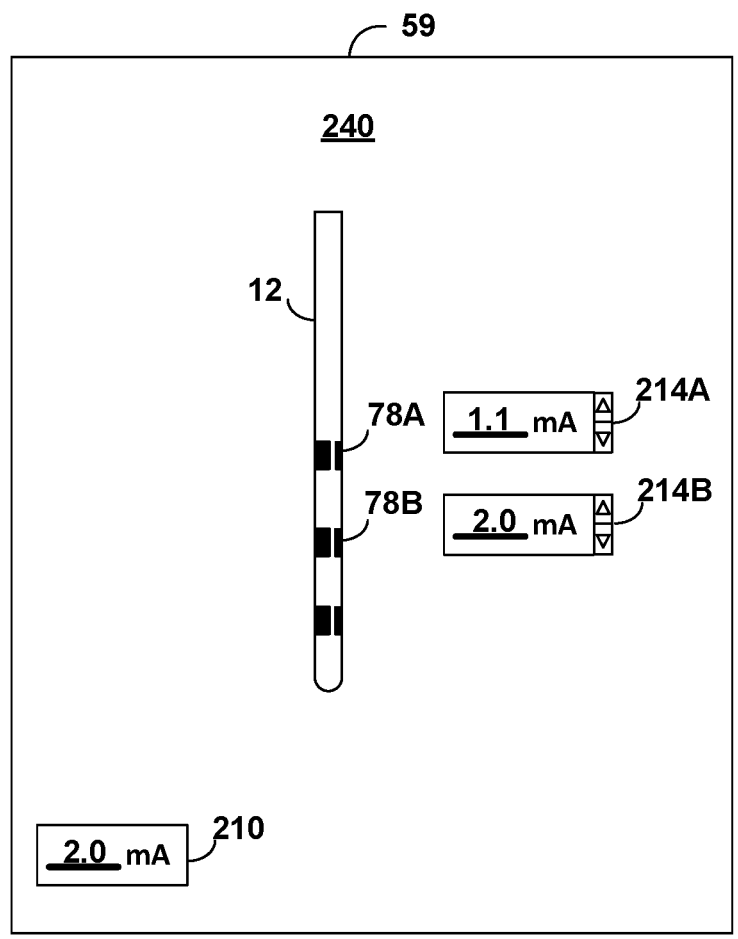
FIG. 10 illustrates an example programmer screens, in accordance with this disclosure.

FIG. 10 is an example user interface screens of programmer 40. In the example of FIG. 10, user interface 59 of programmer 40 may numerically display the stimulation amplitude associated with an electrode. In this example, FIG. 10 illustrates a segmented lead, of which segmented electrodes may have stimulation amplitudes adjusted in accordance with various techniques of this disclosure.

In FIG. 10, adjacent electrodes 78A and 78B, two numbers are depicted. In some examples, the top number of field 214A may indicate the desired electrical current amplitude to be sourced or sunk by a first electrode, e.g., electrode 78A. The bottom number of field 214B may indicate the stimulation amplitude that is sourced or sunk by a second electrode, e.g., electrode 78B, that in particular illustrative examples of this disclosure, is not the target for adjustment. In some examples, however, both electrodes 78A and 78B or more electrodes may be targets for adjustment. For example, lead 12 may include three electrodes, with two being adjusted in parallel, in accordance with various techniques of this disclosure. FIG. 10 also illustrates window 210 showing the master current amplitude. In an example involving 64 current regulator branches, electrode 78B may implement 64/64 of the branches, whereas electrode 78A may implement 35/64 of the branches (e.g., 35 out of the 64 branches) because 35/64 multiplied by a master current amplitude of 2.0 mA equals ~1.1 mA. As mentioned before, displayed current values may be rounded according to predefined rounding rules, but the actual amplitude may be more or less than the displayed amplitude.

In the example of FIG. 10, user interface 59 also includes input devices, such as up/down arrows, to adjust the desired current amplitude. In some examples, user interface 59 may provide input devices and fillable fields, such that a user may have options for how the user wishes to provide input.

In some examples, processing circuitry 50 may output, for display via a user interface, the first electrical current amplitude in measurement units comprising milliampere measurement units, such as for display via user interface 59. For example, processing circuitry 50 may provide a display value for electrode 78A of '1.09' (pre-rounding) or '1.1' (post-rounding) to a user interface device, such as user interface 59. Processing circuitry 50 may then receive from the user interface device 59 user input defining a desired electrical current amplitude in measurement units comprising milliampere measurement units. For example, a user may desire 2.2 mA with respect to electrode 78A. As such, programmer 40 may transfer the desired electrical current value to processing circuitry 50. Processing circuitry 50 may perform the adjustment in accordance with the various techniques of this disclosure. For example, processing circuitry 50 may increase the master amplitude to 2.2 mA and decrease the fraction associated with electrode 78B from 64/64 to 58/64 to maintain the electrical current amplitude of electrode 78B at 2.0 mA (or 1.99 mA pre-rounding), while achieving the desired electrical current amplitude of 2.2 mA for electrode 78A by also increasing the first fraction from 35/64 to 64/64. Processing circuitry 50 may then output the adjustment to the first electrical current amplitude of the first stimulation pulses in measurement units comprising milliampere measurement units (i.e., 2.2 mA). For example, processing circuitry 50 may output 2.2 mA to programmer 40, such that the milliampere value may be displayed via user interface 59.

In some examples, processing circuitry 50 may also output, for display via user interface 59, fractional values corresponding to the adjustment to the first fraction or the adjustment to the second fraction, wherein the fractional values indicate a change in contribution of the first or second electrodes defining a relative degree to which a respective electrode delivers a desired intensity to a particular zone. A contribution of an electrode is the degree to which a given electrode delivers a desired intensity of a zone. The electrode contribution may have a value between 0.0 and 1.0. Zones may be cathodal (e.g., for stimulation) or anodal (e.g., for shielding/guarding). A "contribution" of an electrode generally refers to the relative degree to which a given electrode delivers a desired intensity to the zone that recruited the electrode. As such, the electrode contribution may have a value between 0.0 and 1.0. Electrode contributions are described in U.S. Pat. No. 8,996,123, entitled, "MANAGING ELECTRICAL STIMULATION THERAPY BASED ON VARIABLE ELECTRODE COMBINATIONS," by Goetz et al., the entire content of which is incorporated herein by reference. For example, display window 240 of FIG. 10 may include fractional, decimal, or percentage values indicating contribution levels. However, because a user is adjusting current amplitudes, the display of fractional, decimal, or percentage values may not provide information that a user may use in adjusting the current values using fields 214 or input devices associated therewith.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The terms "processor," "processing circuitry," or "controller" or may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, ROM, NVRAM, EEPROM, flash memory, magnetic memory, optical media, or the like. The instructions may be executed to support one or more aspects of the functionality described in this disclosure.

Various aspects of the disclosure have been described. These and other aspects are within the scope of the following claims.

The invention claimed is:
1. A neuromodulation system comprising:
a first electrode on a lead, wherein the first electrode is a segmented electrode in a set of segmented electrodes at substantially the same axial position as one another along a length of the lead;
a second electrode;
a stimulation generator configured to deliver first stimulation pulses to the first electrode and second stimulation pulses to the second electrode, wherein a first electrical current amplitude of the first stimulation pulses is a first fraction of a master amplitude and a second electrical current amplitude of the second stimulation pulses is a second fraction of the master amplitude; and
a processor configured to:
generate an initial instruction for the stimulation generator to deliver: (i) the first simulation pulses based on the first fraction of the master amplitude, and (ii) the second stimulation pulses based on the second fraction of the master amplitude;
receive user input comprising a desired electrical current amplitude;
determine that an adjustment to the first electrical current amplitude of the first stimulation pulses is required based on the desired electrical current amplitude;
determine whether the first fraction is at a fraction maximum; and
determine a target adjustment in accordance with at least one of a first target adjustment scheme or a second target adjustment scheme, based at least in part on a comparison of the desired electrical current amplitude to the master amplitude and the determination of whether the first fraction is at the fraction maximum,
wherein, for the first target adjustment scheme, the processor is configured to:

determine, as the target adjustment, an adjustment to at least the first fraction,
wherein, for the second target adjustment scheme, the processor is configured to:
determine, as the target adjustment:
(i) an adjustment to the master amplitude, and
(ii) an adjustment to at least the second fraction relative to the master amplitude adjustment; and
generate, based at least in part on the target adjustment, an adjustment instruction for the stimulation generator to deliver the first stimulation pulses at the desired electrical current amplitude and deliver the second stimulation pulses at approximately the same second electrical current amplitude.

2. The system of claim 1,
wherein to determine that the adjustment to the first electrical current amplitude of the first stimulation pulses is required based on the desired electrical current amplitude, the processor is configured to determine the user input requires an increase to the first electrical current amplitude of the first stimulation pulses; and
wherein to determine, as the target adjustment, the adjustment to at least the first fraction, the processor is configured to determine, when (i) the first fraction is not at the fraction maximum and (ii) the desired electrical current amplitude is less than the master amplitude, that the adjustment to the first fraction includes increasing the first fraction.

3. The system of claim 1,
wherein to determine that the adjustment to the first electrical current amplitude of the first stimulation pulses is required based on the desired electrical current amplitude, the processor is configured to determine the user input requires a decrease to the first electrical current amplitude of the first stimulation pulses; and
wherein to determine, as the target adjustment, the adjustment to at least the first fraction, the processor is configured to determine, when the first fraction is not at the fraction maximum, that the adjustment to the first fraction includes decreasing the first fraction.

4. The system of claim 1,
wherein to determine that the adjustment to the first electrical current amplitude of the first stimulation pulses is required based on the desired electrical current amplitude, the processor is configured to determine the user input requires an increase to the first electrical current amplitude of the first stimulation pulses; and
wherein to determine, as the target adjustment, the adjustment to the master amplitude and the adjustment to at least the second fraction, the processor is configured to determine, when the desired electrical current amplitude is greater than the master amplitude, that:
the adjustment to the master amplitude includes increasing the master amplitude; and
the adjustment to at least the second fraction includes decreasing the second fraction relative to the increase in master amplitude.

5. The system of claim 1,
wherein the fraction maximum is a first fraction maximum,
wherein to determine that the adjustment to the first electrical current amplitude of the first stimulation pulses is required based on the desired electrical current amplitude, the processor is configured to determine the user input requires a decrease to the first electrical current amplitude of the first stimulation pulses; and
wherein to determine, as the target adjustment, the adjustment to the master amplitude and the adjustment to at least the second fraction, the processor is configured to determine, when the first fraction is at the first fraction maximum defined for the first electrode and the second fraction is not at a second fraction maximum defined for the second electrode, that:
the adjustment to the master amplitude includes decreasing the master amplitude; and
the adjustment to at least the second fraction includes increasing the second fraction relative to the decrease in the master amplitude.

6. The system of claim 5, wherein the processor is further configured to:
increase, based on the decrease in the master amplitude, the second fraction by a first amount to maintain the second electrical current amplitude at approximately the same amplitude relative to an original second electrical current amplitude.

7. The system of claim 1, wherein the processor is further configured to:
output, for display via a user interface, the first electrical current amplitude in measurement units comprising milliampere measurement units;
receive, via the user interface, the user input defining the desired electrical current amplitude in measurement units comprising milliampere measurement units; and
output, for display via the user interface, the adjustment to the first electrical current amplitude of the first stimulation pulses in measurement units comprising milliampere measurement units.

8. The system of claim 1, wherein the processor is further configured to:
output, to the stimulation generator as part of the adjustment instruction, fractional values corresponding to the adjustment to the first fraction or the adjustment to the second fraction, wherein the fractional values indicate a change in contribution of the first or second electrodes defining a relative degree to which a respective electrode delivers a desired intensity to a particular zone.

9. The system of claim 1, wherein the fraction maximum is equal to approximately a number of branches of a current regulator available to the set of segmented electrodes divided by a number of electrode segments in the set of segmented electrodes.

10. A method of performing neuromodulation, the method comprising:
generating an initial instruction for a stimulation generator to deliver: (i) first simulation pulses to a first electrode on a lead based on a first fraction of a master amplitude, and (ii) second stimulation pulses to a second electrode based on a second fraction of the master amplitude, wherein the first electrode is a segmented electrode in a set of segmented electrodes at substantially the same axial position as one another along a length of the lead;
receiving user input comprising a desired electrical current amplitude;
determining that an adjustment to the first electrical current amplitude of the first stimulation pulses is required based on the desired electrical current amplitude;
determining whether the first fraction is at a fraction maximum; and
determining a target adjustment in accordance with at least one of a first target adjustment scheme or a second target adjustment scheme, based at least in part on a comparison of the desired electrical current amplitude to the master amplitude, a target adjustment and the determination of whether the first fraction is at the fraction maximum;

performing one of the first target adjustment scheme or the second target adjustment scheme, wherein the first target adjustment scheme includes:
determining, as the target adjustment, an adjustment to at least the first fraction, wherein the second target adjustment scheme includes:
determining, as the target adjustment:
(i) an adjustment to the master amplitude, and
(ii) an adjustment to at least the second fraction relative to the master amplitude adjustment; and generating, based at least in part on the target adjustment, an adjustment instruction for the stimulation generator to deliver the first stimulation pulses at the desired electrical current amplitude and deliver the second stimulation pulses at approximately the same second electrical current amplitude.

11. The method of claim 10,
wherein determining that the adjustment to the first electrical current amplitude of the first stimulation pulses is required based on the desired electrical current amplitude comprises determining the user input requires an increase to the first electrical current amplitude of the first stimulation pulses; and
wherein determining, as the target adjustment, the adjustment to at least the first fraction comprises determining, when (i) the first fraction is not at the fraction maximum and (ii) the desired electrical current amplitude is less than the master amplitude, that the adjustment to the first fraction includes increasing the first fraction.

12. The method of claim 10,
wherein determining that the adjustment to the first electrical current amplitude of the first stimulation pulses is required based on the desired electrical current amplitude comprises determining the user input requires a decrease to the first electrical current amplitude of the first stimulation pulses; and
wherein determining, as the target adjustment, the adjustment to at least the first fraction comprises determining, when the first fraction is not at the fraction maximum, that the adjustment to the first fraction includes decreasing the first fraction.

13. The method of claim 10,
wherein determining that the adjustment to the first electrical current amplitude of the first stimulation pulses is required based on the desired electrical current amplitude comprises determining the user input requires an increase to the first electrical current amplitude of the first stimulation pulses;
and wherein determining, as the target adjustment, the adjustment to the master amplitude and the adjustment to at least the second fraction comprises determining, when the desired electrical current amplitude is greater than the master amplitude, that:
the adjustment to the master amplitude includes increasing the master amplitude; and
the adjustment to the second fraction includes decreasing the second fraction relative to the increase in master amplitude.

14. The method of claim 10,
wherein the fraction maximum is a first fraction maximum;

wherein determining that the adjustment to the first electrical current amplitude of the first stimulation pulses is required based on the desired electrical current amplitude comprises determining the user input requires a decrease to the first electrical current amplitude of the first stimulation pulses;
and wherein determining, as the target adjustment, the adjustment to the master amplitude and the adjustment to at least the second fraction comprises determining, when the first fraction is at the first fraction maximum defined for the first electrode and the second fraction is not at a second fraction maximum defined for the second electrode, that:
the adjustment to the master amplitude includes decreasing the master amplitude; and
the adjustment to the second fraction includes increasing the second fraction relative to the decrease in the master amplitude.

15. The method of claim 14, further comprising:
increasing, based on the decrease in the master amplitude, the second fraction by a first amount to maintain the second electrical current amplitude at approximately the same amplitude relative to an original second electrical current amplitude.

16. The method of claim 10, further comprising:
outputting, for display via a user interface, the first electrical current amplitude in measurement units comprising milliampere measurement units;
receiving, via the user interface, the user input defining the desired electrical current amplitude in measurement units comprising milliampere measurement units; and
outputting, for display via the user interface, the adjustment to the first electrical current amplitude of the first stimulation pulses in measurement units comprising milliampere measurement units.

17. The method of claim 10, further comprising:
outputting, to the stimulation generator as part of the adjustment instruction, fractional values corresponding to the adjustment to the first fraction or the adjustment to the second fraction, wherein the fractional values indicate a change in contribution of the first or second electrodes defining a relative degree to which a respective electrode delivers a desired intensity to a particular zone.

18. The method of claim 10, wherein the fraction maximum is equal to approximately a number of branches of a current regulator available to the set of segmented electrodes divided by a number of electrode segments in the set of segmented electrodes.

19. A non-transitory computer-readable storage medium having stored thereon instructions that, when executed, cause one or more processors to at least:
generate an initial instruction for a stimulation generator to deliver: (i) first simulation pulses to a first electrode on a lead based on a first fraction of a master amplitude, and (ii) second stimulation pulses to a second electrode based on a second fraction of the master amplitude, wherein the first electrode is a segmented electrode in a set of segmented electrodes at substantially the same axial position as one another along a length of the lead;
receive user input comprising a desired electrical current amplitude;
determine that an adjustment to the first electrical current amplitude of the first stimulation pulses is required based on the desired electrical current amplitude;
determine whether the first fraction is at a fraction maximum, wherein the fraction maximum is equal to approximately a number of branches available to the set of segmented electrodes divided by a number of electrode segments in the set of segmented electrodes;

determine a target adjustment in accordance with at least one of a first target adjustment scheme or a second target adjustment scheme, based at least in part on a comparison of the desired electrical current amplitude to the master amplitude, a target adjustment and the determination of whether the first fraction is at the fraction maximum;

perform one of the first target adjustment scheme or the second target adjustment scheme, wherein the first target adjustment scheme includes: determining, as the target adjustment, an adjustment to at least the first fraction, wherein the second target adjustment scheme includes: determining, as the target adjustment:
(i) an adjustment to at least the first fraction, or
(ii) an adjustment to the master amplitude and an adjustment to at least the second fraction relative to the adjustment to the master amplitude; and generate, based at least in part on the target adjustment, an adjustment instruction for the stimulation generator to deliver the first stimulation pulses at the desired electrical current amplitude and deliver the second stimulation pulses at approximately the same second electrical current amplitude.

20. The non-transitory computer-readable storage medium of claim 19, wherein to determine the adjustment to the first electrical current amplitude of the first stimulation pulses is required based on the desired electrical current amplitude, the instructions, when executed, cause the one or more processors to at least determine the user input requires an increase to the first electrical current amplitude of the first stimulation pulses; and wherein the adjustment to at least the first fraction comprises, when (i) the first fraction is not at the fraction maximum and (ii) the desired electrical current amplitude is less than the master amplitude, increasing the first fraction.

21. The non-transitory computer-readable storage medium of claim 19, wherein to determine the adjustment to the first electrical current amplitude of the first stimulation pulses is required based on the desired electrical current amplitude, the instructions, when executed, cause the one or more processors to at least determine the user input requires a decrease to the first electrical current amplitude of the first stimulation pulses; and wherein the adjustment to at least the first fraction comprises, when the first fraction is not at the fraction maximum, decreasing the first fraction.

22. The non-transitory computer-readable storage medium of claim 19, wherein to determine the adjustment to the first electrical current amplitude of the first stimulation pulses is required based on the desired electrical current amplitude, the instructions, when executed, cause the one or more processors to at least determine the user input requires an increase to the first electrical current amplitude of the first stimulation pulses; and wherein the adjustment to the master amplitude and the adjustment to at least the second fraction comprises, when the desired electrical current amplitude is greater than the master amplitude, and the instructions, when executed, cause the one or more processors to:
increase the master amplitude; and
decrease the second fraction relative to the increase in master amplitude.

23. The non-transitory computer-readable storage medium of claim 19, wherein the fraction maximum is equal to approximately a number of branches of a current regulator available to the set of segmented electrodes divided by a number of electrode segments in the set of segmented electrodes.

* * * * *